United States Patent [19]

Watson et al.

[11] Patent Number: 4,806,141
[45] Date of Patent: * Feb. 21, 1989

[54] HERBICIDAL COMPOUNDS AND COMPOSITIONS

[75] Inventors: Keith G. Watson, Box Hill North; Lynette A. Garson, Parkville; Graham J. Bird, North Melbourne; Graeme J. Farquharson, Reservoir, all of Australia

[73] Assignee: ICI Australia Limited, Melbourne, Australia

[*] Notice: The portion of the term of this patent subsequent to May 19, 2004 has been disclaimed.

[21] Appl. No.: 937,467

[22] Filed: Dec. 2, 1986

Related U.S. Application Data

[63] Continuation of Ser. No. 457,387, Jan. 12, 1983, abandoned.

[30] Foreign Application Priority Data

Jan. 29, 1982 [AU] Australia ............................. PF2489
May 31, 1982 [AU] Australia ............................. PF4228

[51] Int. Cl.$^4$ ........................................... A01N 33/00
[52] U.S. Cl. ..................................... 71/121; 564/256; 71/98; 71/106; 71/107
[58] Field of Search .................. 564/256; 71/98, 106, 71/107, 121; 560/107

[56] References Cited

U.S. PATENT DOCUMENTS 3,950,420  4/1976  Sawaki et al. .................... 564/256
3,989,737  11/1976  Sawaki et al. ........................ 71/98

OTHER PUBLICATIONS

Iwataki et al., *Advances in Pesticide Science* Part 2 (1979) Permagon Press, Publ., pp. 234–243.

*Primary Examiner*—James H. Reamer
*Attorney, Agent, or Firm*—Cushman, Darby & Cushman

[57] ABSTRACT

The invention concerns novel compounds of the formula I

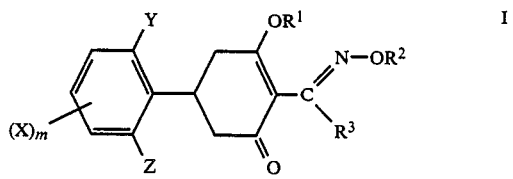

wherein
  Z is selected from hydrogen, halogen, $C_1$ to $C_6$ alkyl, and $C_1$ to $C_6$ alkoxy;
  Y is selected from halogen, $C_1$ to $C_6$ alkyl and $C_1$ to $C_6$ alkoxy;
  X is selected from halogen, $C_1$ to $C_6$ alkyl and $C_1$ to $C_6$ alkoxy and if Y is methyl and Z is hydrogen or methyl then at least one of X is not methyl;
  $R^1$ is selected from hydrogen, alkyl, alkenyl, alkynyl, substituted alkyl, alkylsulfonyl, arylsulfonyl, acyl and an inorganic or organic cation;
  $R^2$ is selected from alkyl, substituted alkyl, alkenyl, haloalkenyl, alkynyl and haloalkynyl;
  $R^3$ is selected from alkyl, fluoroalkyl, alkenyl, alkynyl and phenyl; and
  m is an integer chosen from 1 to 3.

The compounds are cereal selective herbicides and in further embodiments the invention provides processes for the preparation of compounds of formula I, intermediates useful in the preparation of compounds of formula I, herbicidal compositions containing as active ingredient a compound of formula I, and processes for severely damaging or killing unwanted plants by applying to the plants or to the growth medium of the plants an effective amount of a compound of formula I.

13 Claims, No Drawings

HERBICIDAL COMPOUNDS AND COMPOSITIONS

This is a continuation of application Ser. No. 457,387, filed Jan. 12, 1983, which was abandoned upon the filling hereof.

This invention relates to organic compounds having biological activity and in particular to organic compounds having herbicidal properties, to processes for the preparation of such compounds, to intermediates useful in the preparation of such compounds and to herbicidal compositions and processes utilizing such compounds.

The use of certain cyclohexane-1,3-dione derivatives as grass herbicides is known in the art. For example, the "Pesticide Manual" (C R Worthing Editor, The British Crop Protection Council, 6th Edition 1979) describes the cyclohexane-1,3-dione derivative known commercially as alloxydim-sodium (methyl 3-[1-allyloxyimino)-butyl]-4-hydroxy-6,6-dimethyl-2-oxocyclohex-3-ene-carboxylate) and its use as a grass herbicide. This compound is disclosed in Australian Pat. No. 464 655 and its equivalents such as UK Pat. No. 1 461 170 and U.S. Pat. No. 3 950 420.

More recently, at the 1980 British Crop Protection Conference ("1980 British Crop Protection Conference—Weeds, Proceedings Vol 1, Research Reports", pp 39 to 46, British Crop Protection Council, 1980), a new cyclohexane-1,3-dione grass herbicide code named NP 55 (2-(N-ethoxybutrimidoyl)-5-(2-ethylthiopropyl)-3-hydroxy-2-cyclohexen-1-one) was announced. This compound is disclosed in Australian Patent Application No. AU-A1-35,314/78 and its equivalents.

As indicated above, both alloxydim-sodium and NP 55 are grass herbicides, that is, herbicides which selectively control the growth of grass weeds (monocotyledonous plants) in broad-leaved crops (dicotyledonous plants).

At the 1978 International Union of Pure and Applied Chemistry Fourth International Congress of Pesticide Chemistry ("Advances in Pesticide Science—Part 2", pp 235–243, Pergamon Press, 1979), in a paper discussing the chemical structure and herbicidal activity of alloxydim-sodium, Iwataki and Hirono made the following disclosure about the herbicidal selectivity between wheat and oats of certain 5-phenyl substituted cyclohexane-1,3-dione derivatives:

"When substituted phenyl groups were introduced at the C-5 position (Table 6), the selectivity between wheats and oats such as *Avena fatua* and *Avena sativa* was observed. The selectivity was found only in the case of para-substituents at the phenyl nucleus and the effect was not found in the case of di- or tri-substitution. Even in the para-substituents, the degree of activity or selectivity was different. The best result was obtained when the methyl group was introduced at the para-position and the hydroxy or the methoxy derivative gave moderately good results."

It has now been found that certain 5-phenyl substituted cyclohexane-1,3-dione derivatives in which the phenyl ring has three or more substituents, one of which is in the 2- or ortho-position of the ring, exhibit particularly useful cereal selective herbicidal activity.

Accordingly the invention provides a compound of formula I:

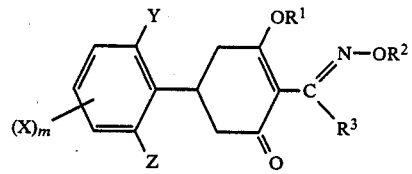

wherein:

Z is chosen from the group consisting of hydrogen, halogen, $C_1$ to $C_6$ alkyl and $C_1$ to $C_6$ alkoxy;

Y is chosen from the group consisting of halogen, $C_1$ to $C_6$ alkyl and $C_1$ to $C_6$ alkoxy;

X, which may be the same or different if there is more than one X, is chosen from the group consisting of halogen, $C_1$ to $C_6$ alkyl and $C_1$ to $C_6$ alkoxy and if Y is methyl and Z is hydrogen or methyl then at least one of X is not methyl;

$R^1$ is chosen from the group consisting of: hydrogen, $C_1$ to $C_6$ alkyl; $C_2$ to $C_6$ alkenyl; $C_2$ to $C_6$ alkynyl; substituted $C_1$ to $C_6$ alkyl wherein the alkyl group is substituted with a substituent chosen from the group consisting of $C_1$ to $C_6$ alkoxy, $C_1$ to $C_6$ alkylthio, phenyl and substituted phenyl wherein the benzene ring is substituted with from one to three substituents chosen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; $C_1$ to $C_6$ (alkyl) sulfonyl; benzenesulfonyl; substituted benzenesulfonyl wherein the benzene ring is substituted with from one to three substituents chosen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; an acyl group; and an inorganic or organic cation;

$R^2$ is chosen from the group consisting of $C_1$ to $C_6$ alkyl; $C_2$ to $C_6$ alkenyl; $C_2$ to $C_6$ haloalkenyl; $C_2$ to $C_6$ alkynyl; $C_2$ to $C_6$ haloalkynyl; substituted $C_1$ to $C_6$ alkyl wherein the alkyl group is substituted with a substituent chosen from the group consisting of halogen, $C_1$ to $C_6$ alkoxy, $C_1$ to $C_6$ alkylthio, phenyl and substituted phenyl wherein the benzene ring is substituted with from one to three substituents chosen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio;

$R^3$ is chosen from the group consisting of $C_1$ to $C_6$ alkyl; $C_1$ to $C_6$ fluoroalkyl; $C_2$ to $C_6$ alkenyl; $C_2$ to $C_6$ alkynyl; and phenyl;

when Z is hydrogen m is an integer selected from 2 and 3; and when Z is a substituent other than hydrogen m is an integer selected from 1 to 3.

When in the compound of formula I $R^1$ is chosen from acyl the nature of the acyl group is not narrowly critical. Although not intending to be bound by theory, it is believed that when $R^1$ is acyl the acyl group is removed in the plant by hydrolysis to give the corresponding compound of formula I in which $R^1$ is hydrogen. Suitable acyl groups include: alkanoyl, for example $C_2$ to $C_6$ alkanoyl; aroyl, for example benzoyl and substituted benzoyl wherein the benzene ring is substituted with from one to three substituents chosen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; and heteroaroyl, for example 2-furoyl, 3-furoyl, 2-thenoyl and 3-thenoyl.

When in the compound of formula I $R^1$ is chosen from an inorganic or organic cation the nature of the cation is not narrowly critical. Although not intending to be bound by theory, it is believed that when $R^1$ is a cation the cation is removed in the plant to give a compound of formula I wherein $R^1$ is hydrogen. Suitable inorganic cations include the alkali and alkaline earth metal ions, heavy metal ions including the transition metal ions, and the ammonium ion. Suitable organic cations include the cation $R^4R^5R^6R^7N^\oplus$ wherein $R^4$, $R^5$, $R^6$ and $R^7$ are independently chosen from the group consisting of: hydrogen; $C_1$ to $C_{10}$ alkyl; substituted $C_1$ to $C_{10}$ alkyl wherein the alkyl group is substituted with a substituent chosen from the group consisting of hydroxy, halogen and $C_1$ to $C_6$ alkoxy; phenyl; benzyl; and the groups substituted phenyl and substituted benzyl wherein the benzene ring is substituted with from one to three substituents chosen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio.

It should be recognized that when $R^1$ is hydrogen the compounds of the invention may exist in any one of three tautomeric forms as shown below:

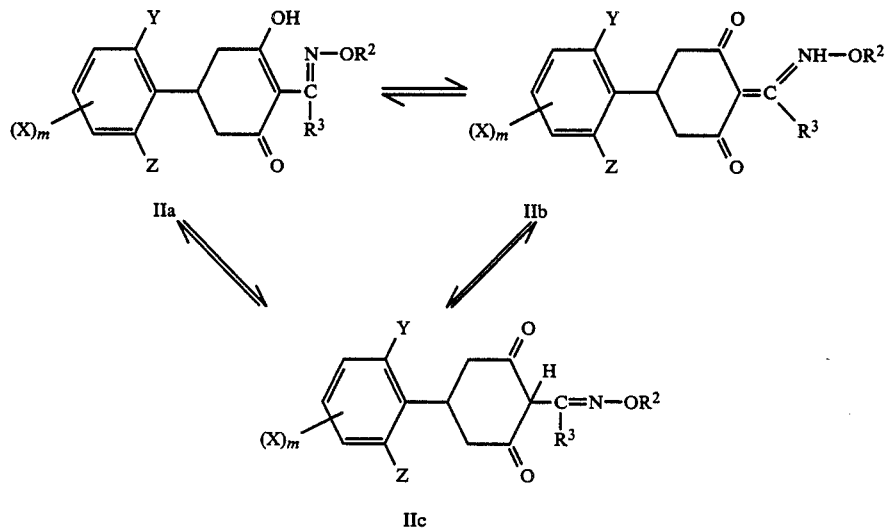

Suitable Z include hydrogen, halogen, $C_1$ to $C_6$ alkyl and $C_1$ to $C_6$ alkoxy.

Suitable Y include halogen, $C_1$ to $C_6$ alkyl and $C_1$ to $C_6$ alkoxy.

Suitable X include halogen, $C_1$ to $C_6$ alkyl and $C_1$ to $C_6$ alkoxy provided that at least two of Z, Y and X are methyl and that if Y is methyl and Z is hydrogen or methyl then at least one of X is not methyl.

Suitable $R^1$ include hydrogen, benzoyl, substituted benzoyl wherein the benzene ring is substituted with from one to three substituents selected from the group consisting of halogen, nitro, $C_1$ to $C_6$ alkyl, $C_1$ to $C_6$ alkoxy and $C_1$ to $C_6$ haloalkyl, and the group M wherein M is an alkali metal ion.

Suitable $R^2$ include $C_1$ to $C_6$ alkyl, $C_2$ to $C_6$ alkenyl, $C_2$ to $C_6$ alkynyl, benzyl and substituted benzyl wherein the benzene ring is substituted with from one to three substituents selected from the group consisting of halogen, nitro, $C_1$ to $C_6$ alkyl, $C_1$ to $C_6$ alkoxy and $C_1$ to $C_6$ haloalkoxy.

Suitable $R^3$ include $C_1$ to $C_6$ alkyl.

When Z is hydrogen suitable m are selected from 2 and 3 when Z is a substituent other than hydrogen suitable m are selected from 1 to 3.

Preferred Z include hydrogen, halogen, $C_1$ to $C_4$ alkyl and $C_1$ to $C_4$ alkoxy.

Preferred Y include halogen, $C_1$ to $C_4$ alkyl and $C_1$ to $C_4$ alkoxy.

Preferred X include halogen, $C_1$ to $C_4$ alkyl and $C_1$ to $C_4$ alkoxy.

Preferred $R^1$ include: hydrogen; $C_2$ to $C_6$ alkanoyl such as acetyl; benzoyl and substituted benzoyl wherein the benzene ring is substituted with from one to three substituents selected from the group consisting of halogen, nitro, $C_1$ to $C_6$ alkyl and $C_1$ to $C_6$ alkoxy, benzenesulfonyl and substituted benzenesulfonyl wherein the benzene ring is substituted with from one to three substituents selected from the group consisting of halogen, nitro, $C_1$ to $C_6$ alkyl and $C_1$ to $C_6$ alkoxy; and an inorganic or organic cation selected from the cations of the alkali metals such as lithium, potassium and sodium, the cations of the alkaline earth metals such as magnesium, calcium and barium, the cations of the transition metals such as manganese, copper, zinc, iron, nickel, cobalt and silver, the ammonium ion and the tri- and tetra-(alkyl)ammonium ions wherein alkyl is selected from $C_1$ to $C_6$ alkyl and $C_1$ to $C_6$ hydroxyalkyl.

Preferred $R^2$ include: $C_1$ to $C_6$ alkyl; $C_2$ to $C_6$ alkenyl; $C_2$ to $C_6$ alkynyl; $C_1$ to $C_6$ haloalkyl; $C_2$ to $C_6$ haloalkenyl; and $C_2$ to $C_6$ haloalkynyl.

Preferred $R^3$ include $C_1$ to $C_6$ alkyl.

More preferred compounds of the invention include those compounds of formula I in which the benzene ring is substituted in the 2-, 4- and 6-positions. That is, compounds of formula

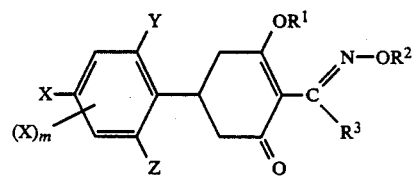

wherein:

Z and Y are independently selected from the group consisting of fluorine, chlorine, bromine, methyl, ethyl, methoxy and ethoxy;

X is selected from the group consisting of fluorine, chlorine, bromine, $C_1$ to $C_4$ alkyl and $C_1$ to $C_4$ alkoxy;

at least two of Z, Y and X are methyl and if Z and Y are both methyl then at least one of X is not methyl;

$R^1$ is selected from the group consisting of hydrogen, acetyl, benzoyl, nitrobenzoyl, methylbenzenesulfonyl and the cations of the alkali metals;

$R^2$ is selected from the group consisting of $C_1$ to $C_3$ alkyl, allyl and propargyl;

$R^3$ is selected from $C_1$ to $C_3$ alkyl; and m is selected from 0, 1 and 2.

Even more preferred compounds of the invention include those compounds of formula I in which the benzene ring is substituted in the 2-, 4- and 6-positions and the substituent in the 4-position is methyl. That is, compounds of formula

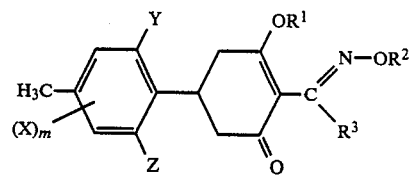

wherein:

Z and Y are independently selected from the group consisting of fluorine, chlorine, bromine, methyl and methoxy;

X is selected from the group consisting of fluorine, chlorine, bromine, methyl, ethyl and methoxy;

at least one of Z, Y and X is methyl and if Z and Y are both methyl then at least one of X is not methyl;

$R^1$ is selected from the group consisting of hydrogen, benzoyl, lithium, sodium and potassium;

$R^2$ is selected from ethyl and allyl;

$R^3$ is selected from ethyl and n-propyl; and m is selected from 0, 1 and 2.

Specific examples of the compounds of the invention include those compounds detailed in Table 1 below.

TABLE 1

| Compound No | $(X)_m$ | Y | Z | $R^1$ | $R^2$ | $R^3$ |
|---|---|---|---|---|---|---|
| 1 | 3-$CH_3O$—4-$CH_3$ | $CH_3$ | $CH_3$ | H | $C_2H_5$ | $C_2H_5$ |
| 2 | 4-$CH_3$ | Cl | $CH_3$ | H | $C_2H_5$ | $C_2H_5$ |
| 3 | 4-$CH_3$ | Cl | $CH_3$ | H | $CH_2CH=CH_2$ | $C_2H_5$ |
| 4 | 4-$CH_3$ | $CH_3$ | $CH_3O$ | H | $C_2H_5$ | $C_2H_5$ |
| 5 | 4-$CH_3$ | $CH_3O$ | $CH_3O$ | H | $C_2H_5$ | $C_2H_5$ |
| 6 | 4-$CH_3$ | Br | Br | H | $C_2H_5$ | $C_2H_5$ |
| 7 | 4-Br | $CH_3$ | $CH_3$ | H | $C_2H_5$ | $C_2H_5$ |
| 8 | 3-$C_2H_5$—4-$CH_3$ | $CH_3$ | $CH_3$ | H | $C_2H_5$ | $C_2H_5$ |
| 9 | 3-$C_2H_5$—4-$CH_3$ | $CH_3$ | $CH_3$ | H | $CH_2CH=CH_2$ | $C_2H_5$ |
| 10 | 4-$CH_3$—3-n-$C_4H_9$ | $CH_3$ | $CH_3$ | H | $C_2H_5$ | $C_2H_5$ |
| 11 | 3-Cl—4-$CH_3$ | $CH_3$ | $CH_3$ | H | $C_2H_5$ | $C_2H_5$ |
| 12 | 3-Br—4-$CH_3$ | $CH_3$ | $CH_3$ | H | $C_2H_5$ | $C_2H_5$ |
| 13 | 3-Br—4-$CH_3$ | $CH_3$ | $CH_3$ | H | $CH_2CH=CH_3$ | $C_2H_5$ |
| 14 | 3-F—4-$CH_3$ | $CH_3$ | $CH_3$ | H | $C_2H_5$ | $C_2H_5$ |
| 15 | 3,4-$(CH_3)_2$ | $CH_3$ | $C_2H_5$ | H | $C_2H_5$ | $C_2H_5$ |
| 16 | 4-$C_2H_5$ | $C_2H_5$ | $C_2H_5$ | H | $C_2H_5$ | $C_2H_5$ |
| 17 | 4-$C_2H_5$ | $C_2H_5$ | $C_2H_5$ | $C_6H_5CO$ | $C_2H_5$ | $C_2H_5$ |
| 18 | 4-Cl | Cl | Cl | H | $C_2H_5$ | $C_2H_5$ |
| 19 | 4-$CH_3$ | Cl | $CH_3$ | H | $C_2H_5$ | $C_3H_7$ |
| 20 | 4-$CH_3$ | Cl | $CH_3$ | $CH_3CO$ | $C_2H_5$ | $C_3H_7$ |
| 21 | 4-$CH_3(CH_2)_3O$ | $CH_3$ | $CH_3$ | H | $C_2H_5$ | $C_2H_5$ |
| 22 | 4-$CH_3O$ | $CH_3O$ | $CH_3O$ | $C_6H_5CO$ | $C_2H_5$ | $C_2H_5$ |
| 23 | 4-$CH_3O$ | $CH_3O$ | $CH_3O$ | H | $C_2H_5$ | $C_2H_5$ |
| 24 | 3,4,5-$(CH_3)_3$ | $CH_3$ | $C_2H_5$ | H | $C_2H_5$ | $C_2H_5$ |
| 25 | 3-$C_2H_5$—4,5-$(CH_3)_2$ | $CH_3$ | $CH_3$ | H | $C_2H_5$ | $C_2H_5$ |
| 26 | 3,5-$(C_2H_5)$—4-$CH_3$ | $CH_3$ | $CH_3$ | H | $C_2H_5$ | $C_2H_5$ |
| 27 | 3-Br—4,5-$(CH_3)_2$ | $CH_3$ | $CH_3$ | H | $C_2H_5$ | $C_2H_5$ |
| 28 | 3,5-$(CH_3)_2$—4-$C_2H_5$ | $CH_3$ | $CH_3$ | H | $C_2H_5$ | $C_2H_5$ |
| 29 | 3-Br—4,5-$(CH_3)_2$ | $C_2H_5$ | $CH_3$ | H | $C_2H_5$ | $C_2H_5$ |
| 30 | 4-$CH_3$ | $OCH_3$ | $CH_3$ | H | $CH_2CH=CH_2$ | n-$C_3H_7$ |
| 31 | 4-Br—3,5-$(CH_3)_2$ | $CH_3$ | $CH_3$ | H | $C_2H_5$ | $C_2H_5$ |
| 32 | 4-$CH_3$ | $OCH_3$ | $CH_3$ | H | $C_2H_5$ | n-$C_3H_7$ |
| 33 | 3,5-$Cl_2$—4-$CH_3$ | $CH_3$ | $CH_3$ | H | $C_2H_5$ | $C_2H_5$ |
| 34 | 3-Cl—4-$CH_3$ | $CH_3$ | $CH_3$ | H | $CH_2CH=CH_2$ | $C_2H_5$ |
| 35 | 3-Cl—4-$CH_3$ | $CH_3$ | $CH_3$ | H | $CH_2CH_2F$ | $C_2H_5$ |
| 36 | 3-Cl—4-$CH_3$ | $CH_3$ | $CH_3$ | H | $C_2H_5$ | n-$C_3H_7$ |
| 37 | 3-Cl—4-$CH_3$ | $CH_3$ | $CH_3$ | H | $CH_2CH=CH_2$ | n-$C_3H_7$ |
| 38 | 3-Cl—4-$CH_3$ | $CH_3$ | $CH_3$ | H | $CH_2CH_2F$ | n-$C_3H_7$ |
| 39 | 3-Cl—4-$CH_3$ | $CH_3$ | $OCH_3$ | H | $C_2H_5$ | $C_2H_5$ |
| 40 | 3,4,5-$(CH_3)_3$ | Br | $CH_3$ | H | $C_2H_5$ | $C_2H_5$ |
| 41 | 3-F—4,5-$(CH_3)_2$ | $CH_3$ | $CH_3$ | H | $C_2H_5$ | $C_2H_5$ |
| 42 | 3-F—4,5-$(CH_3)_2$ | $CH_3$ | $CH_3$ | H | $C_2H_5$ | n-$C_3H_7$ |

TABLE 1-continued

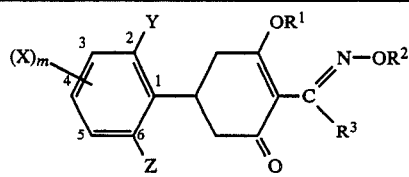

| Compound No | (X)$_m$ | Y | Z | R$^1$ | R$^2$ | R$^3$ |
|---|---|---|---|---|---|---|
| 43 | 3,5-(CH$_3$)$_2$—4-C$_2$H$_5$ | CH$_3$ | CH$_3$ | H | C$_2$H$_5$ | n-C$_3$H$_7$ |
| 44 | 4-CH$_3$ | OC$_2$H$_5$ | CH$_3$ | H | C$_2$H$_5$ | C$_2$H$_5$ |
| 45 | 3-F—4-CH$_3$ | CH$_3$ | CH$_3$ | H | C$_2$H$_5$ | n-C$_3$H$_7$ |
| 46 | 3-Cl—4,5-(CH$_3$)$_2$ | CH$_3$ | CH$_3$ | H | C$_2$H$_5$ | C$_2$H$_5$ |
| 47 | 3-Cl—4,5-(CH$_3$)$_2$ | CH$_3$ | CH$_3$ | H | C$_2$H$_5$ | n-C$_3$H$_7$ |
| 48 | 3-Cl—4,5-(CH$_3$)$_2$ | CH$_3$ | OCH$_3$ | H | C$_2$H$_5$ | C$_2$H$_5$ |
| 49 | 3,4-(CH$_3$)$_2$ | OCH$_3$ | CH$_3$ | H | C$_2$H$_5$ | n-C$_3$H$_7$ |
| 50 | 3,4,5-(CH$_3$)$_3$ | Cl | CH$_3$ | H | C$_2$H$_5$ | n-C$_3$H$_7$ |
| 51 | 3,4-(CH$_3$)$_2$ | OCH$_3$ | CH$_3$ | H | C$_2$H$_5$ | C$_2$H$_5$ |
| 52 | 3-Br—4,5-(CH$_3$)$_2$ | CH$_3$ | CH$_3$ | H | C$_2$H$_5$ | n-C$_3$H$_7$ |
| 53 | 3,4-(CH$_3$)$_2$ | CH$_3$ | OCH$_3$ | H | C$_2$H$_5$ | n-C$_3$H$_7$ |
| 54 | 3,5-Cl$_2$—4-CH$_3$ | CH$_3$ | CH$_3$ | H | C$_2$H$_5$ | n-C$_3$H$_7$ |
| 55 | 3-OCH$_3$—4-CH$_3$ | CH$_3$ | CH$_3$ | H | C$_2$H$_5$ | n-C$_3$H$_7$ |
| 56 | 3,4-(CH$_3$)$_2$ | CH$_3$ | OCH$_3$ | H | C$_2$H$_5$ | C$_2$H$_5$ |
| 57 | 3,5-(CH$_3$)$_2$—4-OCH$_3$ | CH$_3$ | CH$_3$ | H | C$_2$H$_5$ | n-C$_3$H$_7$ |
| 58 | 3,4,5-(CH$_3$)$_3$ | Br | CH$_3$ | H | C$_2$H$_5$ | n-C$_3$H$_7$ |
| 59 | 3,4,5-(CH$_3$)$_3$ | Cl | CH$_3$ | H | C$_2$H$_5$ | C$_2$H$_5$ |
| 60 | 4-CH$_3$ | Br | CH$_3$ | H | C$_2$H$_5$ | n-C$_3$H$_7$ |
| 61 | 3,4,5-(CH$_3$)$_3$ | Br | CH$_3$ | Na$^+$ | C$_2$H$_5$ | n-C$_3$H$_7$ |
| 62 | 3,4,5-(CH$_3$)$_3$ | OCH$_3$ | CH$_3$ | H | C$_2$H$_5$ | n-C$_3$H$_7$ |
| 63 | 3,4,5-(CH$_3$)$_3$ | Cl | CH$_3$ | Na$^+$ | C$_2$H$_5$ | n-C$_3$H$_7$ |
| 64 | 3,4,5-(CH$_3$)$_3$ | F | CH$_3$ | H | C$_2$H$_5$ | n-C$_3$H$_7$ |
| 65 | 3,4-(CH$_3$)$_2$ | CH$_3$ | F | H | C$_2$H$_5$ | n-C$_3$H$_7$ |
| 66 | 3-OCH$_3$—4,5-(CH$_3$)$_2$ | CH$_3$ | CH$_3$ | H | C$_2$H$_5$ | n-C$_3$H$_7$ |
| 67 | 3,4-(CH$_3$)$_2$ | CH$_3$ | Cl | H | C$_2$H$_5$ | n-C$_3$H$_7$ |
| 68 | 3,4-(CH$_3$)$_2$ | CH$_3$ | Br | H | C$_2$H$_5$ | n-C$_3$H$_7$ |
| 69 | 3,4,5-(CH$_3$)$_3$ | Br | CH$_3$ | K$^+$ | C$_2$H$_5$ | n-C$_3$H$_7$ |
| 70 | 3,4,5-(CH$_3$)$_3$ | Br | CH$_3$ | C$_6$H$_5$CO | C$_2$H$_5$ | n-C$_3$H$_7$ |
| 71 | 3,4,5-(CH$_3$)$_3$ | Br | CH$_3$ | ½ Cu$^{2+}$ | C$_2$H$_5$ | n-C$_3$H$_7$ |
| 72 | 3,4,5-(CH$_3$)$_3$ | Br | CH$_3$ | a | C$_2$H$_5$ | n-C$_3$H$_7$ |
| 73 | 3,4,5-(CH$_3$)$_3$ | Cl | CH$_3$ | H | CH$_2$C≡CH | n-C$_3$H$_7$ |
| 74 | 3,4,5-(CH$_3$)$_3$ | OCH$_3$ | CH$_3$ | Li$^+$ | C$_2$H$_5$ | n-C$_3$H$_7$ |
| 75 | 3,4,5-(CH$_3$)$_3$ | OCH$_3$ | CH$_3$ | Na$^+$ | C$_2$H$_5$ | n-C$_3$H$_7$ |
| 76 | 3,4,5-(CH$_3$)$_3$ | OCH$_3$ | CH$_3$ | H | C$_2$H$_5$ | C$_2$H$_5$ |
| 77 | 3,4,5-(CH$_3$)$_3$ | Cl | CH$_3$ | Li$^+$ | C$_2$H$_5$ | n-C$_3$H$_7$ |
| 78 | 3,4,5-(CH$_3$)$_3$ | Cl | CH$_3$ | H | CH$_2$CBr=CH$_2$ | n-C$_3$H$_7$ |
| 79 | 3,4,5-(CH$_3$)$_3$ | OCH$_3$ | CH$_3$ | b | C$_2$H$_5$ | n-C$_3$H$_7$ |
| 80 | 3,4,5-(CH$_3$)$_3$ | OCH$_3$ | CH$_3$ | c | C$_2$H$_5$ | C$_2$H$_5$ |
| 81 | 3,4-(CH$_3$)$_2$—5-Br | CH$_3$ | H | H | C$_2$H$_5$ | n-C$_3$H$_7$ |
| 82 | 3,4,5-(CH$_3$)$_3$ | OCH$_3$ | H | H | C$_2$H$_5$ | n-C$_3$H$_7$ |

Footnotes to TABLE 1
a - (n-C$_4$H$_9$)$_4$N$^\oplus$
b - 4-NO$_2$C$_6$H$_4$CO
c - 4-CH$_3$C$_6$H$_4$SO$_2$ The compounds of the invention may be prepared by a variety of methods and in a further aspect the invention provides methods for the preparation of compounds of formula I.

Conveniently the preparation of the compounds of the invention can be considered in three or four parts.

Part A involves the formation of a 5-(substituted phenyl)cyclohexane-1,3-dione of formula IX. This reaction may be carried out in a two step process by condensing a benzaldehyde derivative of formula V with acetone to form a ketone of formula VI, which is in turn condensed with a malonic acid ester of formula VII to give a 5-(substituted phenyl)cyclohexane-1,3-dione of formula IX, either with or without the isolation of the intermediate of formula VIII.

Alternatively, this preparation may be carried out in a two step process by condensing a benzaldehyde derivative of formula V with a malonic acid ester of formula VII to give a benzylidenemalonate derivative of formula X which is in turn condensed with an acetoacetic acid ester of formula XI to give a 5-(substituted phenyl)-cyclohexane-1,3-dione of formula IX, either with or without isolation of the intermediate of formula XII.

In a further alternative process this preparation may be carried out by condensing a cinnamate of formula XXI with an acetoacetic acid ester of formula XI to give a 5-(substituted phenyl)cyclohexane-1,3-dione of formula IX, either with or without isolation of the intermediate of formula VIII.

The above reaction sequences are set out in SCHEME A parts (i), (ii) and (iii) respectively below, wherein R represents a C$_1$ to C$_6$ alkyl group.

SCHEME A
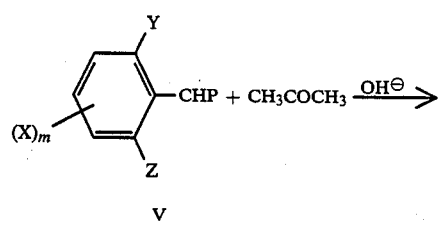
(i)
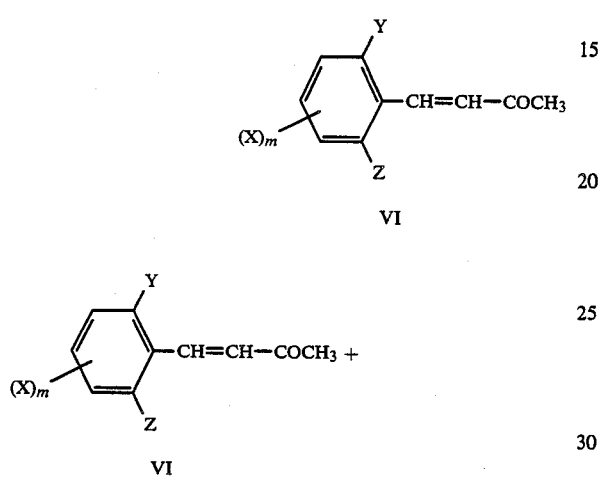
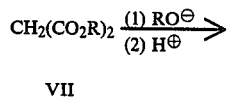
-continued
SCHEME A
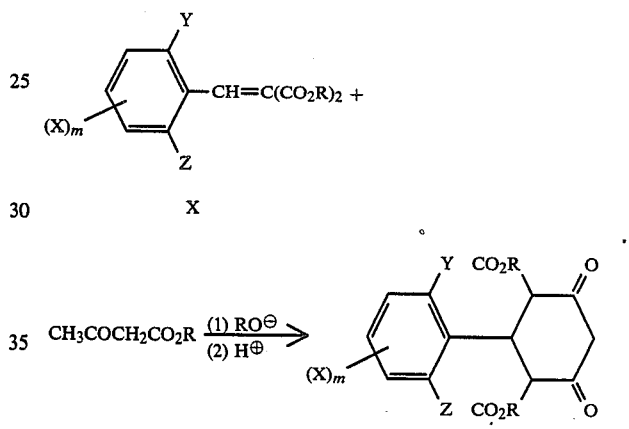
(ii)
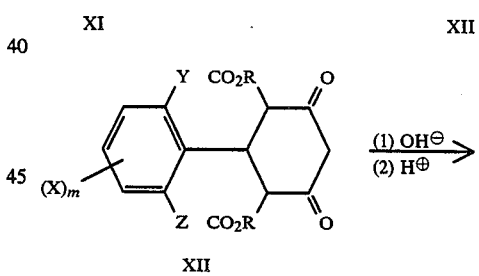
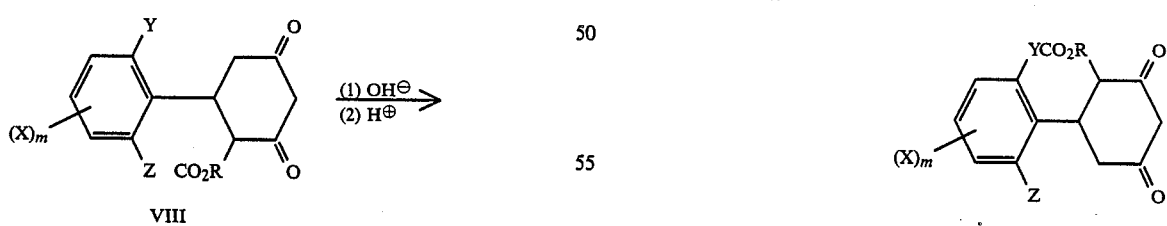
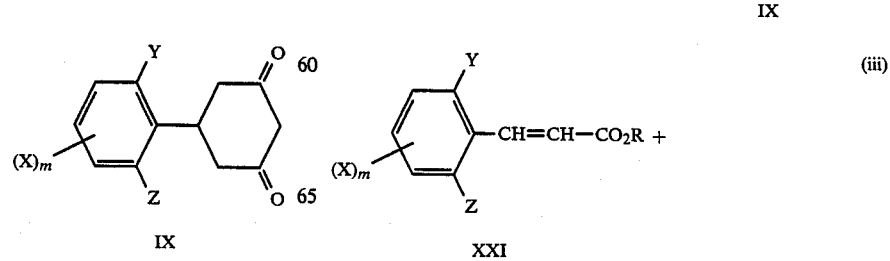
(iii)

-continued
SCHEME A

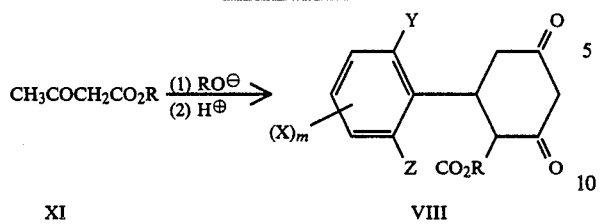

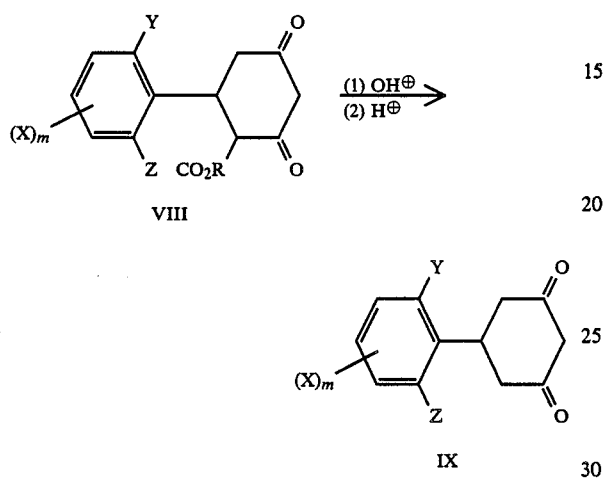

SCHEME B

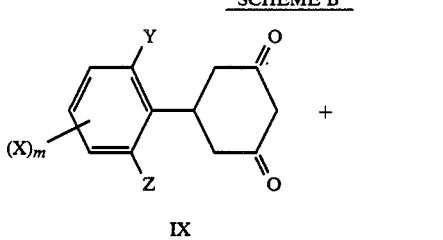

(iv)

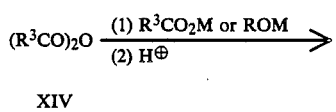

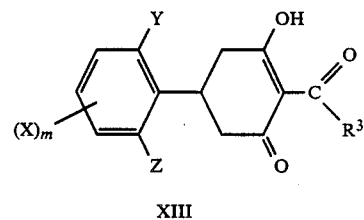

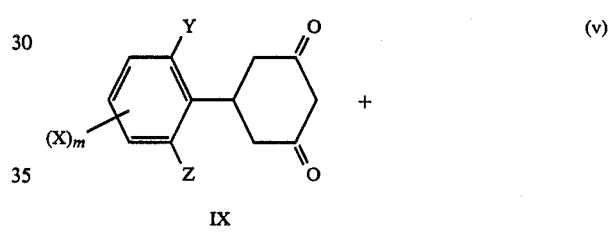

(v)

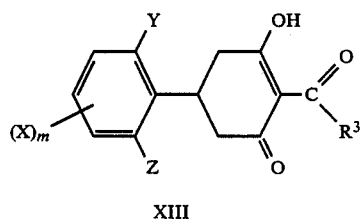

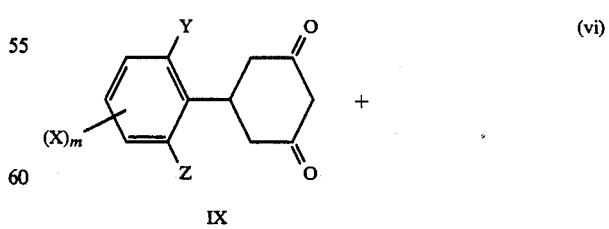

(vi)

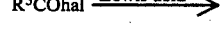

Part B involves the acylation of a compound of formula IX to give a 2-acyl-5-(substituted phenyl)cyclohexane-1,3-dione of formula XIII. This reaction may be carried out by reacting a 5-(substituted phenyl)cyclohexane-1,3-dione of formula IX with:

(iv) a mixture of an acid anhydride of formula XIV and either a salt of that acid or an alkoxide salt wherein M is an alkali metal ion and R is $C_1$ to $C_6$ alkyl;

(v) a mixture of an acid anhydride of formula XIV and the corresponding acid;

(vi) an acid halide of formula XV;

(vii) a mixture of an acid halide of formula XV and the corresponding acid; or (viii) an alkali metal or alkaline earth metal hydride followed by reaction with an acid anhydride of formula XIV or an acid halide of formula XV.

Alternatively this reaction may be carried out by:

(ix) reacting a 5-(substituted phenyl)cyclohexane-1,3-dione of formula IX with an acid halide of formula XV in the presence of pyridine to give an intermediate O-acyl derivative of formula XVI; and then:

(x) reacting the intermediate of formula XVI with a Lewis acid catalyst;

(xi) reacting the intermediate of formula XVI with the corresponding acid of the acid halide of formula XV; or (xii) reacting the intermediate of formula XVI with imidazole.

Each of these reactions is outlined in SCHEME B below wherein hal represents halogen.

-continued
SCHEME B

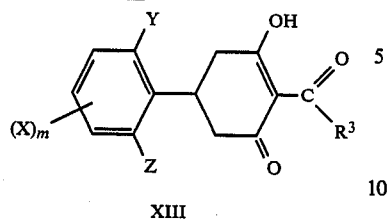

XIII (vii)

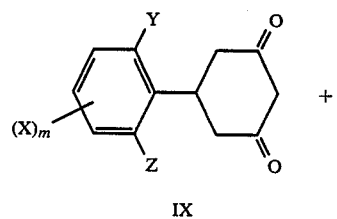

IX $R^3COhal \xrightarrow{R^3CO_2H/H^\oplus}$

XV

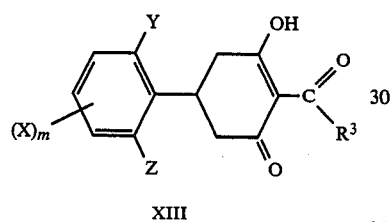

XIII (viii)

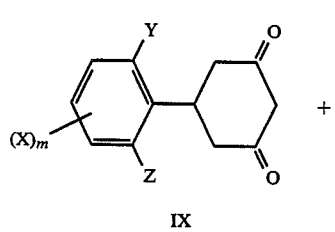

IX $(R^3CO_2)_2O \text{ or } R^3COhal \xrightarrow{(1) H^\ominus}{(2) XIV \text{ or } XV}$

XIV     XV

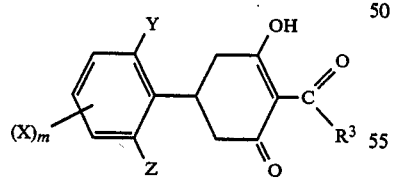

XIII (ix)

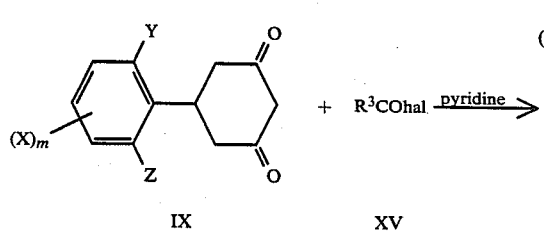

IX                    XV

-continued
SCHEME B

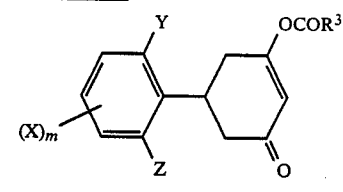

XVI (x)

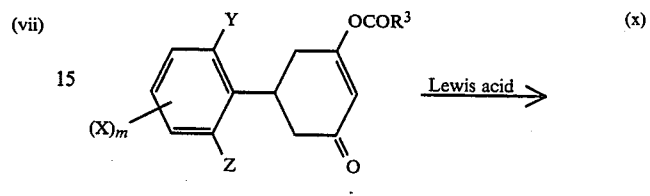 $\xrightarrow{\text{Lewis acid}}$

XVI

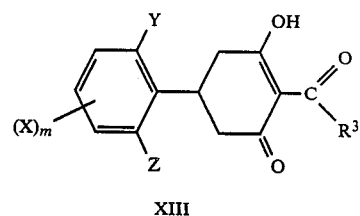

XIII (xi)

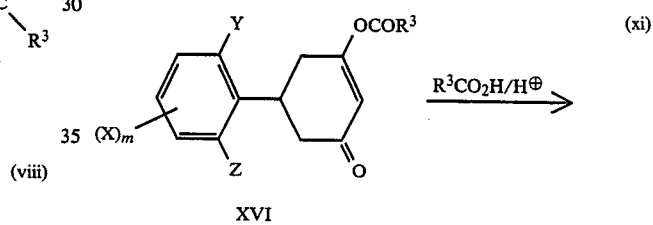 $\xrightarrow{R^3CO_2H/H^\oplus}$

XVI

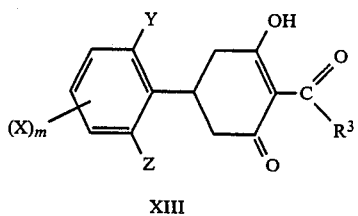

XIII (xii)

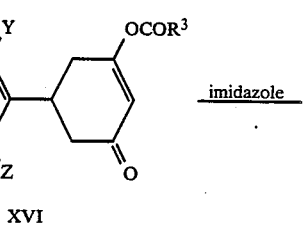 $\xrightarrow{\text{imidazole}}$

XVI

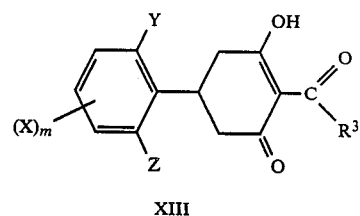

XIII

Part C involves the formation of a compound of the invention of formula I wherein $R^1$ is hydrogen, that is a compound of formula II. This reaction may be carried out either:

(xiii) by reacting a compound of formula XIII with an alkoxyamine derivative of formula XVII to give a compound of formula II; or (xiv) by reacting a compound of formula XIII with hydroxylamine to give an intermediate oxime derivative of formula XVIII and reacting the oxime derivative of formula XVIII with an alkylating agent of formula XIX to give a compound of formula II.

These reaction sequences are set out in SCHEME C below wherein L is a good leaving group such as, for example, chloride, bromide, iodide, sulfate, nitrate, methyl sulfate, ethyl sulfate, tetrafluoroborate, hexafluorophosphate, hexafluoroantimonate, methanesulfonate, fluorosulfonate, fluoromethanesulfonate and trifluoromethanesulfonate.

SCHEME C

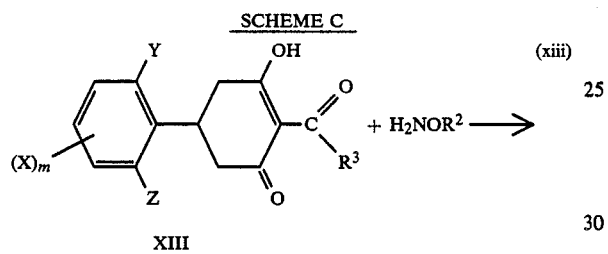

(xiii)

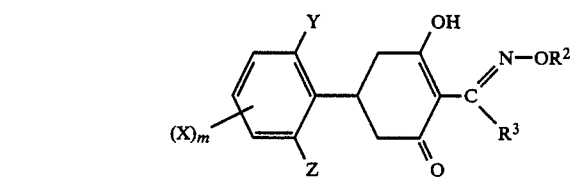

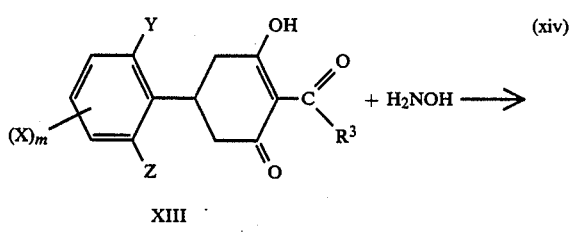

(xiv)

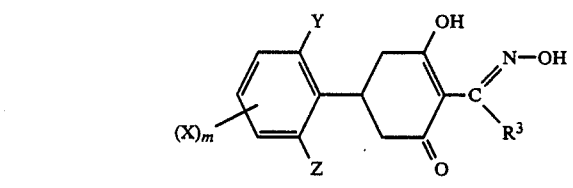

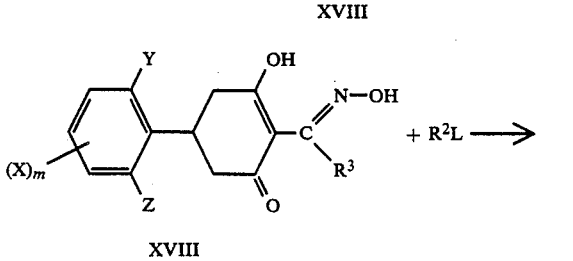

-continued
SCHEME C

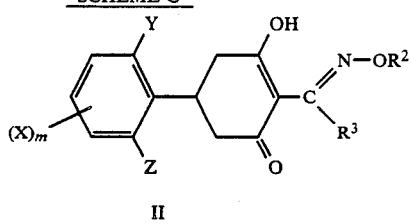

II

Compounds of the invention of formula I wherein $R^1$ is not hydrogen may be prepared from compounds of the invention of formula I wherein $R^1$ is hydrogen, that is, compounds of formula II, by acylation or salt formation as required. This reaction is outlined in SCHEME D below.

SCHEME D

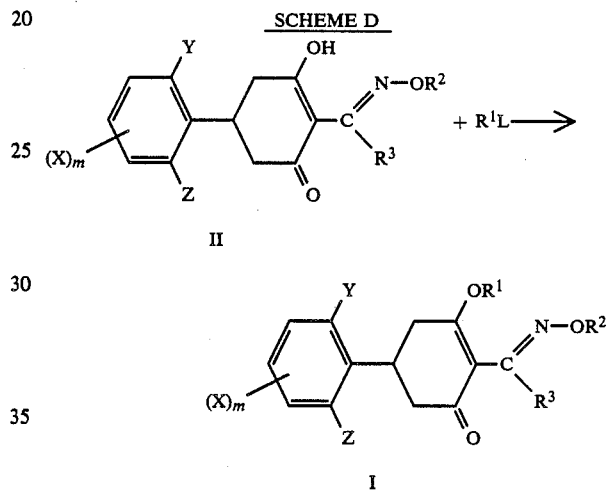

Compounds of the invention of formula I wherein $R^1$ is an inorganic or organic cation may be prepared from the compounds of the invention of formula I wherein $R^1$ is hydrogen, that is, compounds of formula II, by reacting said compounds of formula II with an inorganic or organic salt. For example, the compounds of formula I wherein $R^1$ is an alkali metal ion may be prepared by reacting the appropriate compound of formula II with the appropriate alkali metal hydroxide or alkoxylate. The compounds of formula I wherein $R^1$ is a transition metal ion or an organic cation may similarly be prepared by reacting the appropriate compound of formula II with an appropriate transition metal salt or organic base. Alternatively, the compounds of formula I wherein $R^1$ is a transition metal ion or an organic cation may be prepared by reacting the appropriate compound of formula I wherein $R^1$ is an alkali metal ion with an appropriate transition metal salt or organic salt.

Accordingly, in a further aspect the invention provides a process for the preparation of a compound of formula I, wherein X, Y, Z, $R^1$, $R^2$, $R^3$ and m as hereinbefore defined, which process comprises:

(a) reacting a benzaldehyde derivative of formula V with acetone to give a ketone derivative of formula VI and reacting the ketone derivative of formula VI with a malonic acid ester of formula VII, wherein R is $C_1$ to $C_6$ alkyl, to give a 5-(substituted phenyl)cyclohexane-1,3-dione derivative of formula IX; or reacting a benzaldehyde derivative of formula V with a malonic acid ester of formula VII to give a benzylidenemalonate derivative of formula X and reacting the benzylidenemalonate derivative of formula X with an acetoacetic acid ester of formula XI, wherein R is $C_1$ to $C_6$ alkyl, to give a 5-(substituted phenyl)cyclohexane-1,3-dione derivative of formula IX; or reacting a cinnamate of formula XXI, wherein R is $C_1$ to $C_6$ alkyl, with an acetoacetic acid ester of formula XI, wherein R is $C_1$ to $C_6$ alkyl, to give a 5-(substituted phenyl)cyclohexane-1,3-dione derivative of formula IX;

(b) acylating the 5-(substituted phenyl)cyclohexane-1,3-dione derivative of formula IX with an acid anhydride of formula XIV or an acid halide of formula XV to tive a 2-acyl-5-(substituted phenyl)-cyclohexane-1,3-dione derivative of formula XIII;

(c) reacting the 2-acyl-5-(substituted phenyl)cyclohexane-1,3-dione derivative of formula XIII with an alkoxyamine derivative of formula XVII to give a compound of the invention of formula II or reacting the 2-acyl-5-(substituted phenyl)cyclohexane-1,3-dione derivative of formula XIII with hydroxylamine and alkylating the oxime intermediate of formula XVIII with an alkylating agent of formula XIX, wherein L is a good leaving group, to give a compound of the invention of formula II; and optionally (d) reacting the compound of the invention of formula II with a compound of formula XX, wherein L is a good leaving group, to give a compound of the invention of formula I.

Certain of the intermediate compounds of formulae VI, VIII, IX, X, XII, XXI, XIII, XVI and XVIII are novel compounds and therefore as a further embodiment the invention provides novel compounds of formulae VI, VIII, IX, X, XII, XXI, XIII, XVI and XVIII, wherein the substituents are as hereinbefore defined, and processes for the preparation thereof.

The compounds of formila I are active as herbicides against monocotyledonous weeds, wild grasses, and in particular are selectively active against difficultly controllable wild grasses in crops of cultivated plants. The compounds of the invention are especially useful in the control of wild grasses such as wild oats and rye grass in crops of cultivated monocotyledonous plants such as wheat, barley and other varieties of cereals.

Accordingly, in yet a further aspect the invention provides a process for controlling monocotyledonous weeds in cultivated crops, especially wild grasses in cereal crops such as wheat and barley, which process comprises applying to the crop, or to the growth medium of the crop, a compound of formula I, as hereinbefore defined, in an amount sufficient to severely damage or kill the weeds but insufficient to damage the crop substantially.

As hereinbefore indicated, certain cyclohexane-1,3-dione derivatives, such as those disclosed in Australian Pat. No. 464,655 and Australian Patent Application No. 35,314/78 and numerous other patents and patent applications, are known to be general grass herbicides which show no useful cereal selectivity. Moreover, it is known from the teaching of Iwataki and Hirono ("Advances in Pesticides Science—Part 2", pp 235-243, Pergamon Press, 1979) that some cereal selectivity is observed in such cyclohexane-1,3-dione derivatives when a phenyl group substituted in the para-position is introduced into the 5-position of the cyclohexane ring but the "The selectivity was found only in the case of parasubstituents at the phenyl nucleus and that the effect was not found in the case of di- or tri-substitution". Therefore, it is completely unexpected to find that the cyclohexane-1,3-dione derivatives of the present invention, which have, located in the 5-position of the cyclohexane ring, a phenyl group which is substituted with from three to five substituents, one of which is in an ortho-position, are cereal selective herbicides which effectively control monocotyledonous weeds such as wild oats and rye grass in crops of sensitive, cultivated monocotyledonous plants such as wheat. It is even more surprising to find that those cyclohexane-1,3-dione derivatives of the present invention which have, located in the 5-position of the cyclohexane ring, a phenyl group which is in turn substituted in both the 2- and 6-(ortho-)positions and more preferably in the 2-, 4- and 6-positions, are highly active against monocotyledonous weeds such as wild oats and rye grass at very low rates of application and at the same time are very safe on wheat, a sensitive, cultivated monocotyledonous plant.

The compounds of formula I may be applied directly to the plant (post-emergence application) or to the soil before the emergence of the plant (pre-emergence application). However, the compounds are, in general, more effective when applied to the plant post-emergence.

The compounds of formula I may be used on their own to inhibit the growth of, severely damage, or kill plants but are peferably used in the form of a composition comprising a compound of the invention in admixture with a carrier. Therefore, in yet a further aspect the invention provides plant growth inhibiting, plant damaging, or plant killing compositions comprising a compound of formula I as hereinbefore defined and an inert carrier therefor.

The compositions of the present invention may be in the form of solids, liquids or pastes. The compositions include both dilute compositions which are ready for immediate use and concentrated compositions which may require dilution before use. Therefore, the concentration of the active ingredient in the compositions of the present invention will vary depending on the type of formulation and whether the composition is ready for use such as, for example, a dust formulation or an aqueous emulsion or whether the composition is a concentrate such as, for example, an emulsifiable concentrate or a wettable powder, which is suitable for dilution before use. In general the compositions of the present invention comprise from 1 ppm to 99% by weight of active ingredient.

The solid compositions may be in the form of powders, dusts, pellets, grains, and granules wherein the active ingredient is mixed with a solid diluent. Powders and dusts may be prepared by mixing or grinding the active ingredient with a solid carrier to give a finely divided composition. Granules, grains and pellets may be prepared by bonding the active ingredient to a solid carrier, for example, by coating or impregnating the preformed granular solid carrier with the active ingredient or by agglomeration techniques.

Examples of solid carriers include: mineral earths and clays such as, for example, kaolin, bentonite, kieselguhr, Fuller's earth, Attaclay, diatomaceous earth, bole, loess, talc, chalk, dolomite, limestone, lime, calcium carbonate, powdered magnesia, magnesium oxide, magnesium sulfate, gypsum, calcium sulfate, pyrophyllite, silicic acid, silicates and silica gels; fertilizers such as, for example, ammonium sulfate, ammonium phosphate, ammonium nitrate and urea; natural products of vegetable origin such as, for example, grain meals and flours, bark meals, wood meals, nutshell meals and cellulosic powders; and synthetic polymeric materials such as, for example, ground or powdered plastics and resins.

Alternatively, the solid compositions may be in the form of dispersible or wettable dusts, powders, granules or grains wherein the active ingredient and the solid carrier are combined with one or more surface active agents which act as wetting, emulsifying and/or dispersing agents to facilitate the dispersion of the active ingredient in liquid.

Examples of surface active agents include those of the cationic, anionic and non-ionic type. Cationic surface active agents include quaternary ammonium compounds, for example, the long chain alkylammonium salts such as cetyltrimethylammonium bromide. Anionic surface active agents include: soaps or the alkali metal, alkaline earth metal and ammonium salts of fatty acids; the alkali metal, alkaline earth metal and ammonium salts of ligninsulfonic acid; the alkali metal, alkaline earth metal and ammonium salts of arylsulfonic acids including the salts of naphthalenesulfonic acids such as butylnaphthalenesulfonic acid, the di- and tri-isopropylnaphthalenesulfonic acids, the salts of the condensation products of sulfonated naphthalene and naphthalene derivatives with formaldehyde, the salts of the condensation products of sulfonated naphthalene and naphthalene derivatives with phenol and formaldehyde, and the salts of alkylarylbenzenesulfonic acids such as dodecylbenzenesulfonic acid; the alkali metal, alkaline earth metal and ammonium salts of the long chain mono esters of sulfuric acid or alkylsulfates such as laurylsulfate and the mono esters of sulfuric acid with fatty alcohol glycol ethers. Nonionic surface active agents include: the condensation products of ethylene oxide with fatty alcohols such as oleyl alcohol and cetyl alcohol; the condensation products of ethylene oxide with phenols and alkylphenols such as isooctylphenol, octylphenol and nonylphenol; the condensation products of ethylene oxide with castor oil; the partial esters derived from long chain fatty acids and hexitol anhydrides, for example sorbitan monolaurate, and their condensation products with ethylene oxide; ethylene oxide/propylene oxide block copolymers; lauryl alcohol polyglycol ether acetal; and the lecithins.

The liquid compositions may comprise a solution or dispersion of the active ingredient in a liquid carrier optionally containing one or more surface active agents which act as wetting, emulsifying and/or dispersing agents. Examples of liquid carriers include: water; mineral oil fractions such as, for example, kerosene, solvent naphtha, petroleum, coal tar oils and aromatic hydrocarbons such as, for example, paraffin, cyclohexane, toluene, the xylenes, tetrahydronaphthalene and alkylated naphthalenes; alcohols such as, for example, methanol, ethanol, propanol, isopropanol, butanol, cyclohexanol and propylene glycol; ketones such as, for example, cyclohexanone and isophorone; and strongly polar organic solvents such as, for example, dimethylformamide, dimethylsulfoxide, N-methylpyrrolidone and sulfolane.

A preferred liquid composition comprises an aqueous suspension, dispersion or emulsion of the active ingredient which is suitable for application by spraying, atomizing or watering. Such aqueous compositions are generally prepared by mixing concentrated compositions with water. Suitable concentrated compositions include emulsion concentrates, pastes, oil dispersions, aqueous suspensions and wettable powders. The concentrates are usually required to withstand storage for prolonged periods and after such storage to be capable of dilution with water to form aqueous preparations which remain homogeneous for a sufficient time to enable them to be applied by conventional spray equipment. The concentrates conveniently contain from 20 to 99%, preferably 20 to 60%, by weight of active ingredient.

Emulsion or emulsifiable concentrates are conveniently prepared by dissolving the active ingredient in an organic solvent containing one or more surface active agents. Pastes may be prepared by blending the finely divided active ingredient with a finely divided solid carrier, one or more surface active agents and optionally an oil. Oil dispersions may be prepared by grinding together the active ingredient, a hydrocarbon oil, and one or more surface active agents. Aqueous suspension concentrates may conveniently be prepared by ball milling a mixture of the active ingredient, water, at least one surface active agent and preferably at least one suspending agent. Suitable suspending agents include: hydrophilic colloids such as, for example, poly(N-vinylpyrrolidone), sodium carboxymethylcellulose and the vegetable gums gum acacia and gum tragacanth; hydrated colloidal mineral silicates such as, for example, montmorillonite, beidellite, nontronite, hectorite, saponite, sauconite and bentonite; other cellulose derivatives; and poly(vinyl alcohol). Wettable powder concentrates may conveniently be prepared by blending together the active ingredient, one or more surface active agents, one or more solid carriers and optionally one or more suspending agents and grinding the mixture to give a powder having the required particle size.

The aqueous suspensions, dispersions or emulsions may be prepared from the concentrated compositions by mixing the concentrated compositions with water optionally containing surface active agents and/or oils.

It should be noted that the compounds of the invention of formula I wherein $R^1$ is hydrogen are acidic. Therefore, the compounds of formula I may be formulated and applied as the salts of organic or inorganic bases. In formulating and employing the compounds of formula I in the form of their salts, either the salts per se, that is the compounds of formula I wherein $R^1$ is an inorganic or an organic cation, may be used in the formulation or the compounds of formula I wherein $R^1$ is hydrogen may be used in the formulation and the salts generated in situ by the use of the appropriate organic or inorganic base.

The mode of application of the compositions of the invention will depend to a large extent on the type of composition used and the facilities available for its application. Solid compositions may be applied by dusting or any other suitable means for broadcasting or spreading the solid. Liquid compositions may be applied by spraying, atomizing, watering, introduction into the irrigation water, or any other suitable means for broadcasting or spreading the liquid.

The rate of application of the compounds of the invention will depend on a number of factors including, for example, the compound chosen for use, the identity of the plants whose growth is to be inhibited the formulations selected for use and whether the compound is to be applied for foliage or root uptake. As a general guide, however, an application rate of from 0.005 to 20 kilograms per hectare is suitable while from 0.01 to 5.0 kilograms per hectare may be preferred. The compositions of the invention may comprise, in addition to one or more compounds of the invention, one or more compounds not of the invention but which possess biological activity. For example, as hereinbefore indicated the compounds of the invention are in general substantially more effective against monocotyledonous plants or grass species than against dicotyledonous plants or broad-leaved species. As a result, in certain applications the herbicidal use of the compounds of the invention alone may not be sufficient to protect a crop. Accordingly in yet a still further embodiment the invention provides a herbicidal composition comprising a mixture of at least one herbicidal compound of formula I as hereinbefore defined with at least one other herbicide.

The other herbidide may be any herbicide not having the formula I. It will generally be a herbicide having a complementary action. For example, one preferred class is of mixtures comprising a herbicide active against broad-leaved weeds. A second preferred class is of mixtures comprising a contact herbicide.

Examples of useful complementary herbicides include:

A. benzo-2,1,3-thiadiazin-4-one-2,2-dioxides such as 3-isopropylbenzo-2,1,3-thiadiazin-4one-2,2-dioxide (common name bentazon);

B. hormone herbicides and in particular the phenoxyalkanoic acids such as 4-chloro-2-methylphenoxy acetic acid (common name MCPA), 2-(2,4-dichlorophenoxy)propionic acid (common name dichlorprop), 2,4,5-trichlorophenoxyacetic acid (common name 2,4,5-T), 4-(4-chloro-2-methylphenoxy)butyric acid (common name MCPB), 2,4-dichlorophenoxyacetic acid (common name 2,4-D), 4-(2,4-dichlorophenoxy)butyric acid (common name 2,4-DB), 2-(4-chloro-2-methylphenoxy)-propionic acid (common name mecoprop), and their derivatives (eg salts, esters, amides and the like);

C. 3-[4-(4-halophenoxy)phenyl]-1,1-dialkylureas such as 3-[4-(4-chlorophenoxy)phenyl]-1,1-dimethylurea (common name chloroxuron);

D. dinitrophenols and their derivatives (eg acetates) such as 2-methyl-4,6-dinitrophenol (common name DNOC), 2-tertiarybutyl-4,6-dinitrophenol (common name dinoterb), 2-secondarybutyl-4,6-dinitrophenol (common name dinoseb) and its ester dinoseb acetate;

E. dinitroaniline herbicides such as N',N'-diethyl-2,6-dinitro-4-trifluoromethyl-m-phenylenediamine (common name dinitramine), 2,6-dinitro-N,N-dipropyl-4-trifluoromethylaniline (common name trifluralin) and 4-methylsulfonyl-2,6-dinitro-N,N-dipropylaniline (common name nitralin);

F. phenylurea herbicides such as N'-(3,4-dichlorophenyl)-N,N-dimethylurea (common name diuron) and N,N-dimethyl-N'-[3-(trifluoromethyl)phenyl]urea (common name fluometuron);

G. phenylcarbamoyloxyphenylcarbamates such as 3-[(methoxycarbonyl)amino]phenyl (3-methylphenyl)carbamate (common name phenmedipham) and 3-[(ethoxycarbonyl)amino]phenyl phenylcarbamate (common name desmedipham);

H. 2-phenylpyridazin-3-ones such as 5-amino-4-chloro-2-phenylpyridazin-3-one (common name pyrazon);

I. uracil herbicides such as 3-cyclohexyl-5,6-trimethyleneuracil (common name lenacil), 5-bromo-3-sec-butyl-6-methyluracil (common name bromacil) and 3-tert-butyl-5-chloro-6-methyluracil (common name terbacil);

J. triazine herbicides such as 2-chloro-4-ethylamino-6-(iso-propylamino)-1,3,5-triazine (common name atrazine), 2-chloro-4,6-di(ethylamino)-1,3,5-triazine (common name simazine) and 2-azido-4-(iso-propylamino)-6-methylthio-1,3,5-triazine (common name aziproptryne);

K. 1-alkoxy-2-alkyl-3-phenylurea herbicides such as 3-(3,4-dichlorophenyl)-1-methoxy-1-methylurea (common name linuron), 3-(4-chlorophenyl)-1-methoxy-1-methylurea (common name monolinuron) and 3-(4-bromo-4-chlorophenyl)-1-methoxy-1-methylurea (common name chlorobromuron);

L. thiolcarbamate herbicides such as S-propyl dipropylthiocarbamate (common name verolate);

M. 1,2,4-triazin-5-one herbicides such as 4-amino-4,5-dihydro-3-methyl-6-phenyl-1,2,4-traizine-5-one (common name metamitron) and 4-amino-6-tert-butyl-4,5-dihydro-3-methylthio-1,3,4-triazin-5-one (common name metribuzin);

N. benzoic acid herbicides such as 2,3,6-trichlorobenzoic acid (common name 2,3,6-TBA), 3,6-dichloro-2-methoxybenzoic acid (common name dicamba) and 3-amino-2,5-dichlorobenzoic acid (common name chloramben);

O. anilide herbicides such as N-butoxymethyl-$\alpha$-chloro-2',6'-diethylacetanilide (common name butachlor), the corresponding N-methoxy compound (common name alachlor), the corresponding N-iso-propyl compound (common name propachlor) and 3',4'-dichloropropionanilide (common name propanil);

P. dihalobenzonitrile herbicides such as 2,6-dichlorobenzonitrile (common name dichlobenil), 3,5-dibromo-4-hydroxybenzonitrile (common name bromoxynil) and 3,5-diiodo-4-hydroxybenzonitrile (common name ioxynil);

Q. haloalkanoic herbicides such as 2,2-dichloropropionic acid (common name dalapon), trichloroacetic acid (common name TCA) and salts thereof;

R. diphenylether herbicides such as 4-nitrophenyl 2-nitro-4-trifluoromethylphenyl ether (common name fluorodifen), methyl 5-(2,4-dichlorophenoxy)-2-nitrobenzoate (common name bifenox), 2-nitro-5-(2-chloro-4-trifluoromethylphenoxy)benzoic acid and 2-chloro-4-trifluoromethylphenyl 3-ethoxy-4-nitrophenyl ether;

S. N-(heteroarylaminocarbonyl)benzenesulfonamides such as 2-chloro-N-[(4-methoxy-6-methyl-1,3,5-triazin-2-yl)aminocarbonyl]benzenesulfonamide (commonly known as DPX 4189); and T. miscellaneous herbicides including N,N-dimethyldiphenylacetamide (common name diphenamid), N-(1-naphthyl)phthalamic acid (common name naptalam) and 3-amino-1,2,4-triazole.

Examples of useful contact herbicides include:

U. bipyridylium herbicices such as those in which the active entity is the 1,1'-dimethyl-4,4'-dipyridylium ion (common name paraquat) and those in which the active entity is the 1,1'-ethylene-2,2'-dipyridylium ion (common name diquat);

V. organoarsenical herbicides such as monosodium methanearsonate (common name MSMA); and W. amino acid herbicides such as N-(phosphonomethyl)glycine (common name glyphosate) and its salts and esters.

The invention is now illustrated by, but in no way limited to the following Examples.

EXAMPLE 1

This Example details the preparation of the benzaldehydes of formula V which were used in the preparation of the compounds of the invention of formula I.

Method A

The benzaldehydes were prepared by direct formylation of the benzene ring following the general method described by A Rieche et al (Organic Synthesis, Vol 5, page 49). The products were characterized by proton magnetic resonance spectroscopy and the details are recorded in Table 2 below.

Method B

The benzaldehydes were prepared from the corresponding anilines following the general method described by W F Beech et al (Journal of the Chemical Society, 1954, page 1297) and S D Jolad et al (Organic Synthesis, Vol 5, page 139). The products were characterized by proton magnetic resonance spectroscopy and the details are recorded in Table 2 below.

Method C 2,6-Dimethoxy-4-methylbenzaldehyde was prepared by the method described by D D Ribley et al (Australian Journal of Chemistry, 1968, Vol 21, page 2979). The compound was obtained as an oil and was characterized by its proton magnetic resonance spectrum, the details of which are recorded in Table 2 below.

Method D

Synthesis of 6-methoxy-2,4-dimethylbenzaldehyde and 4-n-butoxy-2,6-dimethylbenzaldehyde.

(a) 3,5-Dimethylphenol (40.0 g; 330 mmole) was dissolved in dichloromethane (210 ml) and the solution was cooled to a temperature of 0° C. Titanium tetrachloride (105 g; 553 mmole) was added dropwise over a period of 5 minutes to the stirred solution and then the temperature of the solution was maintained at 0° C. for a period of 30 minutes while dichloromethyl methyl ether (31.6 g) was added dropwise. The solution was warmed to room temperature and stirred for a period of 30 minutes and then warmed to 35° C. and stirred for a further 15 minutes. The reaction mixture was poured onto ice (ca 300 g) and the aqueous mixture was extracted with dichloromethane. The organic phase was washed three times with water and the solvent was removed by evaporation under reduced pressure. The residue was steam distilled and the distillate was extracted with dichloromethane and the organic phase was separated, dried over anhydrous magnesium sulfate, and the solvent was evaporated under reduced pressure to give 2,4-dimethyl-6-hydroxybenzaldehyde (31.0 g; 63.0%) as a yellow solid mp <50° C. Proton magnetic resonance spectrum (CDCl$_3$; δ in ppm): 2.19 (3H, s); 2.42 (3H, s); 6.41–6.52 (2H, m); 10.05 (1H, s); 11.90 (1H, s).

The residue remaining on completion of the steam distillation was cooled and the solid was collected to give 2,6-dimethyl-4-hydroxybenzaldehyde (7.5 g; 15.0%) as a yellow crystalline solid, mp 190° C. Proton magnetic resonance spectrum (D$_6$-acetone; δ in ppm): 2.53 (6H, s); 6.58 (2H, s); 10.39 (1H, s).

(b) Dimethylsulfate (16.4 g; 130 mmole) and potassium carbonate (20.7 g; 150 mmole) were added to a solution of 2,4-dimethyl-6-hydroxybenzaldehyde (20.0 g; 130 mmole) in acetone (200 ml). The mixture was heated under reflux with stirring for 48 hours and then evaporated to dryness. The residue was dissolved in dichloromethane and washed successively with water, aqueous sodium hydroxide (1M) and water, and then was dried over anhydrous sodium sulfate. The solvent was evaporated under reduced pressure to give 2,4-dimethyl-6-methoxybenzaldehyde (18.9 g; 89.0%). The product was obtained as a brown oil and was characterized by its proton magnetic resonance spectrum, the details of which are recorded in Table 2 below.

(c) 1-Iodobutane (9.2 g; 50 mmole) and potassium carbonate (6.9 g; 50 mmole) were added to a solution of 2,6-dimethyl-4-hydroxybenzaldehyde (7.5 g; 50 mmole) in methyl ethyl ketone (150 ml). The mixture was heated under reflux with stirring for 20 hours and then evaporated to dryness. The residue was dissolved in dichloromethane and washed with water, then dried over anhydrous sodium sulfate. The solvent was evaporated under reduced pressure to give 4-butoxy-2,6-dimethylbenzaldehyde (9.4 g; 92.0%). The product was obtained as a yellow oil and was characterized by its proton magnetic resonance spectrum, the details of which are recorded in Table 2 below.

Method E

The benzaldehydes were commercially available and were used as purchased without further purification.

TABLE 2

| Benzaldehyde Precursors to the Compounds of Formula I |||| 
| Benzaldehyde Derivative | Method | Appearance | Proton Chemical Shift δ in ppm (CDCl$_3$) |
| --- | --- | --- | --- |
| 3-CH$_3$O 2,4,6-(CH$_3$)$_3$ | A | Yellow oil | 2.25(3H,s); 2.48(6H,s); 3.67(3H,s); 6.87(1H,s): 10.44(1H,s). |
| 2-Cl—4,6(CH$_3$)$_2$ | B | Solid, mp <50° C. | 2.34(3H,s); 2.57(3H,s); 6.96(1H,s); 7.12(1H,s); 10.59(1H,s). |
| 6-CH$_3$O— 2,4-(CH$_3$)$_2$ | D | Brown oil | 2.31(3H,s); 2.53(3H,s); 3.84(3H,s); 6.49–6.63 (2H,m); 10.56(1H,s). |
| 2,6-(CH$_3$O)$_2$—4-CH$_3$ | C | Colourless crystals, mp 90–91° C. | 2.34(3H,s); 3.83(6H,s); 6.35(2H,s); 10.41(1H,s). |
| 2,6-Br$_2$—4-CH$_3$ | B | Yellow oil | Not recorded$^a$ |
| 4-Br—2,6-(CH$_3$)$_2$ | B | Yellow oil | 2.50(6H,s); 6.80(2H,s); 10.40(1H,s). |
| 3-C$_2$H$_5$—2,4,6-(CH$_3$)$_3$ | A | Oil bp 85–86° C. 0.7 mm Hg | Not recorded |
| 3-n-C$_4$H$_9$— 2,4,6-(CH$_3$)$_3$ | A | Yellow oil | 1.00(3H,t); 1.40(4H,m); 2.15(3H,s); 2.45–2.60 (8H,m); 6.80(1H,s); 10.48(1H,s). |
| 3-Cl—2,4,6-(CH$_3$)$_3$ | A | Pale brown solid mp <50° C. | 2.40(3H,s); 2.50(3H,s); 2.60(3H,s); 6.80(1H,s); 10.42(1H,s). |
| 3-Br—2,4,6-(CH$_3$)$_3$ | A | Yellow solid, mp 70° C. | 2.40(3H,s); 2.48(3H,s); 2.70(3H,s); 6.95(1H,s); 10.45(1H,s). |
| 3-F—2,4,6-(CH$_3$)$_3$ | A | Yellow oil | 2.28(3H,d); 2.50(6H,s & d); 6.83(1H,d); 10.44 (1H,s). |
| 6-C$_2$H$_5$—2,3,4-(CH$_3$)$_3$ | A | Yellow oil | 1.20(3H,t); 2.10(3H,s); 2.15(3H,s); 2.23(3H,s); 2.90(2H,q); 6.90(1H,s); 10.50(1H,s). |
| 2,4,6-(C$_2$H$_5$)$_3$ | A | Yellow | 1.20(9H,t); 2.60(4H,q); |

TABLE 2-continued
Benzaldehyde Precursors to the Compounds of Formula I

| Benzaldehyde Derivative | Method | Appearance | Proton Chemical Shift δ in ppm (CDCl₃) |
|---|---|---|---|
| | | oil | 2.98(2H,q); 6.88(2H,s); 10.45(1H,s). |
| 2,4,6-Cl₃ | B | Oil | 7.40(2H,s); 10.39(1H,s). |
| 4-n-C₄H₉O—2,6-(CH₃)₂ | D | Yellow oil | 0.97(3H,t); 1.25-1.99 (4H,m); 2.53(6H,s); 3.95(2H,t); 6.55(2H,s); 10.42(1H,s). |
| 2,4,6-(CH₃O)₃ | E | | Not recorded |
| 6-C₂H₅—2,3,4,5-(CH₃)₄ | A | Oil | 1.20(3H,t); 2.20(9H,m); 2.40(6H,s); 2.85(2H,q); 10.55(1H,s). |
| 5-C₂H₅—2,3,4,6-(CH₃)₄ | A | Yellow oil | 1.10(3H,t); 2.20(3H,s); 2.25(3H,s); 2.38(3H,s); 2.42(3H,s); 2.70(2H,q); 10.60(1H,s). |
| 2,4,6-(CH₃)₃—3,5-(C₂H₅)₂ | A | Yellow oil | 1.10(6H,t); 2.25(6H,s); 2.22(3H,s); 2.70(4H,q); 10.60(1H,s). |
| 2-Br—3,4,5,6-(CH₃)₄ | A | Yellow solid, mp 191° C. | Not recorded |
| 2-F—3,4,5,6-(CH₃)₄ | A | Yellow solid, mp 99° C. | Not recorded |
| 2-F—4,5,6-(CH₃)₃ | A | Yellow solid, mp <50° C. | 2.17(3H,s); 2.33(3H,s); 2.55(3H,s); 6.81(1H,d); 10.47(1H,s). |
| 2-Cl—4,5,6-(CH₃)₃ | A | Yellow solid, mp 60-65° C. | 2.17(3H,s); 2.30(3H,s); 2.47(3H,s); 7.09(1H,s); 10.57(1H,s). |
| 2-Br—4,5,6-(CH₃)₃ | A | Colourless solid, mp 66° C. | Not recorded |
| 2-OCH₃—3,4,5,6-(CH₃)₄ | A | Yellow oil, slowly solidified | 2.38(9H,m); 2.51(3H,s); 3.78(3H,s); 10.59 (1H,s). |
| 2-OCH₃—3,4,5-(CH₃)₃ | A | Yellow oil | 2.24(6H,s); 2.29(3H,s); 3.82(3H,s); 7.49(1H,s); 10.32(1H,s). |
| 2-Cl—3,4,5,6-(CH₃)₄ | A | Colourless crystalline solid | 2.20(3H,s); 2.29(3H,s); 2.36(3H,s); 2.41(3H,s); 10.57(1H,s). |
| 2,3,5,6-(CH₃)₄—4-C₂H₅ | A | Colourless solid, mp <50° C. | 1.10(3H,t); 2.20(6H,s); 2.40(6H,s); 2.70(2H,q); 10.55 (1H,s). |
| 2-C₂H₅—3-Br—4,5,6-(CH₃)₃ | A | Yellow solid, mp <50° C. | 1.10(3H,t); 2.10(3H,s); 2.15(3H,s); 2.21(3H,s); 2.52(2H,q); 10.22(1H,s). |
| 4-Br—2,3,5,6-(CH₃)₄ | A | Yellow solid, mp 193° C. | Not recorded |
| 3,5-Cl₂—2,4,6-(CH₃)₃ | A | Oil | 2.55(9H,m); 10.51(1H,s). |
| 3-Cl—2,4-(CH₃)₂—6-OCH₃ | A | Colourless solid, mp 106° C. | 2.40(3H,s); 2.64(3H,s); 3.84(3H,s); 6.72(1H,s); 10.52(1H,s). |
| 3-F—2,4,5,6-(CH₃)₄ | A | Cream solid, mp 110° C. | 2.22(6H,s); 2.45(6H,s); 10.62(1H,s). |
| 2-OC₂H₅—4,6-(CH₃)₂ | D | Yellow solid, mp 52° C. | Not recorded |
| 3-Cl—2,4,5,6-(CH₃)₄ | A | Yellow solid, mp 172-174° C. | Not recorded |
| 3-Cl—2,4,5-(CH₃)₃—6-OCH₃ | A | Colourless solid, mp 60° C. | 2.20(3H,s); 2.36(3H,s); 2.56(3H,s); 3.72(3H,s); 10.36(1H,s). |
| 2-OCH₃—3,4,6-(CH₃)₃ | A | Yellow oil | 2.38(6H,s); 2.52(3H,s); 3.78(3H,s); 6.80(1H,s); 10.57(1H,s). |
| 3-Br—2,4,5,6-(CH₃)₄ | A | Colourless solid, mp 194° C. | Not recorded |
| 2,3,4-(CH₃)₃—6-OCH₃ | A | Yellow oil | 2.34(3H,s); 2.38(3H,s); 2.51(3H,s); 3.84(3H,s); 6.65(1H,s); 10.56(1H,s). |
| 2,3,5,6-(CH₃)₄—4-OCH₃ | A | Colourless solid, mp <50° C. | 2.20(6H,s); 2.38(6H,s); 3.68(3H,s); 10.52(1H,s). |
| 2-Br—4,6-(CH₃)₂ | B | Yellow solid | 2.33(3H,s); 2.56(3H,s); 7.00(1H,s); 7.35(1H,s); 10.50(1H,s). |
| 3-OCH₃—2,4,5,6-(CH₃)₄ | A | Colourless solid, mp <50° C. | 2.18(3H,s); 2.24(3H,s); 2.40(3H,s); 2.42(3H,s); 3.60(3H,s); 10.52(1H,s). |
| 5-Br—2,3,4-(CH₃)₃ | A | Yellow oil | 2.20(6H,s); 2.42(3H,s); 6.73(1H,s); 10.35(1H,s). |

Footnote to Table 2:
ᵃThe benzaldehyde was not purified but was used, as prepared, in the next step of the reaction sequence.

EXAMPLE 2

2-[1-(Ethoxyimino)propyl]-3-hydroxy-5-(3-methoxy-2,4,6-trimethylphenyl)cyclohex-2-en-1-one (1)

(i) An aqueous solution of 2% sodium hydroxide (16.5 ml) was added dropwise over a period of 5 minutes to a suspension of 3-methoxy-2,4,6-trimethylbenzaldehyde (23.5 g) in acetone (21.3 g) and water (13 ml). The mixture was stirred at a temperature of 65° C. for a period of 4 hours and then extracted with dichloromethane. The organic extract was washed several times with water, dried over anhydrous sodium sulfate and the solvent was removed by evaporation under reduced pressure. The product, 1-(3-methoxy-2,4,6-trimethylphenyl)-but-1-en-3-one, was obtained as a viscous oil (28.0 g). Proton magnetic resonance spectrum (CDCl₃; δ in ppm): 2.25 (6H, s); 2.36 (3H, s); 3.67 (3H, s); 6.27 (1H, d); 7.16 (1H, s); 7.61 (1H, d).

(ii) Diethyl malonate (21.0 g) was added to a solution of sodium metal (3.02 g) in anhydrous absolute ethanol (55 ml) and the mixture was heated to reflux temperature. 1-(3-Methoxy-2,4,6-trimethylphenyl)but-1-en-3-one (27.3 g) was added over a period of 2 minutes and the mixture was heated under reflux for a period of 2 hours. An aqueous solution of sodium hydroxide (16.0 g in 100 ml of water) was added and the mixture was heated under reflux for a further 4½ hours. The aqueous mixture was cooled and washed with dichloromethane and the aqueous phase was warmed, acidified with dilute aqueous hydrochloric acid and extracted with ethyl acetate. The ethyl acetate phase was washed with water, dried over anhydrous sodium sulfate and the solvent evaporated under reduced pressure to give 3-hydroxy-5-(3-methoxy-2,4,6-trimethylphenyl)cyclohex-2-en-1-one (20.5 g) as a colourless crystalline solid, mp 165°–166° C.

(iii) Method (a)

A mixture of propionic anhydride (4.0 ml) and propionic acid (4.0 ml) was added to 3-hydroxy-5-(3-methoxy-2,4,6-trimethylphenyl)cyclohex-2-en-1-one (2.0 g) and the mixture was heated at 115° C. with stirring until a clear solution was obtained. Trifluoromethanesulfonic acid (10 drops) was then added and the heating and stirring was continued for a further 2 hours. The mixture was cooled, poured into water, basified with sodium hydroxide and stirred at room temperature for 30 minutes. The aqueous mixture was then acidified to pH 6.0 with dilute hydrochloric acid and extracted with diethyl ether. The ether phase was washed successively with water, dilute aqueous sodium bicarbonate and water, then dried over anhydrous sodium sulfate and evaporated to give a crude red oil (2.3 g). Purification by column chromatography over silica gel (eluant dichloromethane) gave 3-hydroxy-5-(3-methoxy-2,4,6-trimethylphenyl)-2-propionylcyclohex-2-en-1-one (1.35 g; 55.0%) as a pale yellow oil. Proton magnetic resonance spectrum (CDCl$_3$; δ in ppm): 1.15 (3H, t); 2.23 (3H, s); 2.33 (6H, s); 2.35–4.00 (7H, m); 3.66 (3H, s); 6.84 (1H, s); 18.24 (1H, s).

(iii) Method (b)

3-Hydroxy-5-(3-methoxy-2,4,6-trimethylphenyl)-cyclohex-2-en-1-one (3.12 g; 12.0 mmole) was added to a solution of sodium hydride (0.47 g of 60% w/w; 12.0 mmole) in dry dimethylformamide (10 ml) under an atmosphere of nitrogen. The mixture was stirred until a solution had been obtained and then propionic anhydride (1.74 g) was added dropwise and the mixture was heated to 120° C. The mixture was stirred at 120° C. under nitrogen for a period of 2 hours and then the solvent was evaporated under reduced pressure. The mixture was poured into water, basified with sodium hydroxide and stirred at room temperature for 30 minutes. The aqueous mixture was then acidified to pH 6.0 with dilute hydrochloric acid and extracted with diethyl ether. The ether phase was washed successively with water, dilute aqueous sodium bicarbonate and water, then dried over anhydrous sodium sulfate and evaporated to give a crude brown oil (2.2 g). Purification by column chromatography over silica gel (eluant dichloromethane) gave 3-hydroxy-5-(3-methoxy-2,4,6-trimethylphenyl)-2-propionylcyclohex-2-en-1-one (1.0 g; 26.4%) as a pale yellow oil, identical to that obtained by Method (a) above.

(iv) Ethoxyamine hydrochloride (0.43 g) and then aqueous sodium hydroxide (0.18 g in 10.0 ml of water) were added to a solution of 3-hydroxy-5-(3-methoxy-2,4,6-trimethylphenyl)-2-propionylcyclohex-2-en-1-one (1.35 g) in anhydrous absolute ethanol (200 ml). The mixture was stirred at room temperature for a period of 4 hours and then the ethanol was removed by evaporation under reduced pressure. The residue was treated with dichloromethane and the organic phase was washed twice with dilute aqueous hydrochloric acid and twice with water. The organic phase was dried over anhydrous sodium sulfate and the solvent was removed by evaporation under reduced pressure to give 2-[1-(ethoxyimino)propyl]-3-hydroxy-5-(3-methoxy-2,4,6-trimethylphenyl)cyclohex-2-en-1-one (1.40 g), as a pale yellow oil which slowly solidified on standing. Proton magnetic resonance spectrum (CDCl$_3$; δ in ppm): 1.20 (3H, t); 1.32 (3H, t); 2.23 (3H, s); 2.34 (6H, s); 2.35–4.00 (7H, m); 3.65 (3H, s); 4.12 (2H, q); 6.83 (1H, s); 14.95 (1H, s).

EXAMPLE 3

Compounds No 2, 4, 5, 6, 7, 8, 10, 11, 12, 14, 15, 16, 18, 21, 23, 24, 25, 26, 27, 28, 29, 31, 33, 39, 40, 41, 44, 46, 48, 51, 56, 59 and 76 were prepared from the appropriate benzaldehyde derivative following essentially the same procedure as that described in Example 2. The majority of the compounds were obtained as oils and were characterized by and can be identified by their nuclear magnetic resonance spectra. For convenience proton nuclear magnetic resonance spectroscopic data is recorded in Table 5, Example 20.

EXAMPLE 4

Compounds No 19, 32, 36, 42, 43, 45, 47, 49, 50, 52, 53, 54, 55, 57, 60, 62, 64, 65, 66, 67, 68, 81 and 82 were prepared from the appropriate benzaldehyde derivative following essentially the same procedure as that described in Example 2, except that butyric anhydride was used in place of propionic anhydride. The majority of the compounds were obtained as oils and were characterized by and can be identified by their nuclear magnetic resonance spectra. For convenience proton nuclear magnetic resonance spectroscopic data is recorded in Table 5, Example 20.

EXAMPLE 5

2-[1-(Allyloxyimino)propyl]-3-hydroxy-5-(3-bromo-2,4,6-trimethylphenyl)cyclohex-2-en-1-one (13)

Allyloxyamine hydrochloride (0.17 g) and then a solution of sodium hydroxide (0.06 g) in water (1 ml) were added to a stirred mixture of 3-hydroxy-2-propionyl-5-(3-bromo-2,4,6-trimethylphenyl)cyclohex-2-en-1-one (0.50 g, 1.37 mmole) and 95% ethanol. The progress of the reaction was monitored using thin layer chromatography on silica gel (eluant dichloromethane). On completion of the reaction the ethanol was removed by evaporation under reduced pressure and the residue was extracted with dichloromethane. The organic extract was washed with aqueous 5% hydrochloric acid and then with water and dried over anhydrous magnesium sulfate. The solvent was removed by evaporation under reduced pressure to give the product, 2-[1-(allyloxyimino)propyl]-3-hydroxy-5-(3-bromo-2,4,6-trimethylphenyl)cyclohex-2-en-1-one (0.33 g, 57.4%) as an oil.

The product was characterized by proton nuclear magnetic resonance spectroscopy and the specroscopic data is recorded in Table 5, Example 20.

EXAMPLE 6

Compounds No 3, 9, 34 and 35 (see Table 1) were prepared from the appropriate 3-hydroxy-2-propionyl-5-(substituted phenyl)cyclohex-2-en-1-one and the appropriate hydroxylamine hydrochloride following essentially the same procedure as that described in Example 5. The compounds were obtained as oils and were characterized by, and can be identified by their nuclear magnetic resonance spectra. The spectroscopic data is recorded in Table 5, Example 20.

EXAMPLE 7

Compounds No 30, 37, 38, 73 and 78 (see Table 1) were prepared from the appropriate 2-butyryl-3-hydroxy-5-(substituted phenyl)cyclohex-2-en-1-one and the appropriate hydroxylamine hydrochloride following essentially the same procedure as that described in Example 5. The compounds were obtained as oils and were characterized by, and can be identified by their nuclear magnetic resonance spectra. The spectroscopic data is recorded in Table 5, Example 20.

EXAMPLE 8

3-Benzoyloxy-2-[1-(ethoxyimino)propyl]-5-(2,4,6-trimethoxyphenyl)cyclohex-2-en-1one (22)

Aqueous 1% sodium hydroxide solution (6.1 ml) was added to a solution of 2-[1-(ethoxyimino)propyl]-3-hydroxy-5-(2,4,6-trimethoxyphenyl)cyclohex-2-en-1-one (0.52 g; 1.40 mmole) in acetone (25 ml). The mixture was stirred at room temperature for a period of 5 minutes and then benzoyl chloride (0.21 g) was added dropwise. The mixture was stirred for a further period of 15 minutes and then the solvent was removed by evaporation under reduced pressure. The product was purified by chromatography over silica gel (eluant dichloromethane) to give 3-benzoyloxy-2-[1-(ethoxyimino)propyl]-5-(2,4,6-trimethoxyphenyl)cyclohex-2-en-1-one (0.50 g; 73.9%) as a pale yellow solid, mp 139° C.

The product was characterized by proton nuclear magnetic resonance spectroscopy and spectroscopic data is recorded in Table 5, Example 20.

EXAMPLE 9

Compounds No 17, 20, 70 and 79 were prepared from compounds No 16, 19, 58 and 62 and the appropriate acid chloride following essentially the same procedure as that described in Example 8. Each of the products were characterized by proton nuclear magnetic resonance spectroscopy and spectroscopic data is recorded inTable 5, Example 20.

EXAMPLE 10

Sodium salt of 2-[1-(ethoxyimino)butyl]-3-hydroxy-5-(2-chloro-3,4,5,6-tetramethylphenyl)cyclohex-3-en-1-one (63)

A solution of sodium hydroxide (0.10 g) in water (1.0 ml) was added to a solution of 2-[1-(ethoxyimino)butyl]-3-hydroxy-5-(2-chloro-3,4,5,6-tetramethylphenyl)cyclohex-2-en-1-one (1.00 g) in acetone (30 ml). The solvent was removed under reduced pressure and the residue was washed with diethyl ether to give the title compound (0.42 g, 40%) as a colourless solid, mp 250° C.

EXAMPLE 11

Compounds No 61 and 75 (see Table 1) were prepared from the appropriate 2-[1-(ethoxyimino)butyl]-3-hydroxy-5-(substituted phenyl)cyclohex-2-en-1-one derivative and sodium hydroxide following essentially the same procedure as that described in Example 10. The products were solids and their melting points are recorded in Table 5, Example 20.

EXAMPLE 12

Potassium salt of 2[-1-(ethoxyimino)butyl]-3-hydroxy-5-(2-bromo-3,4,5,6-tetramethylphenyl)cyclohex-2-en-1-one (69)

Compound No 69 was prepared from 2-[1-(ethoxyimino)butyl]-3-hydroxy-5-(2-bromo-3,4,5,6-tetramethylphenyl)cyclohex-2-en-1-one and potassium hydroxide following essentially the same procedure as that described in Example 10. The product was a solid and its melting point is recorded in Table 5, Example 20.

EXAMPLE 13

Copper salt of 2-[1-(ethoxyimino)butyl]-3-hydroxy-5-(2-bromo-3,4,5,6-tetramethylphenyl)cyclohex-2-en-1-one (71)

2-[1-(Ethoxyimino)butyl]-3-hydroxy-5-(2-bromo-3,4,5,6-tetramethylphenyl)cyclohex-2-en-1-one (0.39 g, 0.89 mmole) in diethyl ether (50 ml) was shaken with a saturated aqueous cupric acetate solution (50 ml). The mixture was then evaporated to dryness under reduced pressure. The solid residue was washed successively with hot water, cold water and diethyl ether, then dried to give the title compound (0.34 g, 41%) as a pale green solid, mp 213° C.

EXAMPLE 14

Tetrabutylammonium salt of 2-[1-(ethoxyimino)butyl]-3-hydroxy-5-(2-bromo-3,4,5,6-tetramethylphenyl)cyclohex-2-en-1-one (72)

To a solution of 2-[1-(ethoxyimino)butyl]-3-hydroxy-5-(2-bromo-3,4,5,6-tetramethylphenyl)cyclohex-2-en-1-one (0.32 g; 0.73 mmole) in methanol (5 ml) was added a 25% methanolic solution of tetra-n-butylammonium hydroxide (2 ml). The mixture was kept at room temperature for 3 hours and then evaporated to dryness under reduced pressure using a rotary evaporator. The residue was taken up in dichloromethane (50 ml) and water (25 ml). The layers were separated and the organic layer washed with water (2×10 ml), dried over anhydrous sodium sulfate and evaporated under reduced pressure to afford the title compound (0.42 g; 85%), as a brown oil. The product was characterized by proton magnetic resonance spectroscopy and the spectroscopic data is reported in Table 5, Example 20.

EXAMPLE 15

Lithium salt of 2-[1-(ethoxyimino)butyl]-3-hydroxy-5-(2-chloro-3,4,5,6-tetramethylphenyl)cyclohex-2-en-1-one (77)

To a solution of 2-[1-(ethoxyimino)butyl]-3-hydroxy-5-(2-chloro-3,4,5,6-tetramethylpheny)cyclohex-2-en-1-one (0.50 g; 1.26 mmole) in methanol (30 ml) was added a methanolic solution of lithium methoxide (2.0 ml, 1.26 mmole). The mixture was stirred at room temperature for 10 minutes and then evaporated to dryness under reduced pressure. The residue was collected and washed with diethyl ether to give the title compound (0.40 g, 80%), as a colourless solid, mp 250° C.

EXAMPLE 16

Compound No 74 (see Table 1) was prepared from 2-[1-(ethoxyimino)butyl]-3-hydroxy-5-(2-methoxy-3,4,5,6-tetramethylphenyl)cyclohex-2-en-1-one following essentially the same procedure as that described in Example 15. The product was a solid and its melting point is recorded in Table 5, Example 20.

EXAMPLE 17

3-(4-Toluenesulfonyl)oxy-2-[1-(ethoxyimino)propyl]-5-(2-methoxy-3,4,5,6-tetramethylphenyl)cyclohex-2-en-1-one (80)

A solution of sodium ethoxide (1.10 mmole) in ethanol (8.2 ml) was added to a solution of 2-[1-(ethoxyimino)propyl]-3-hydroxy-5-(2-methoxy-3,4,5,6-tetramethylphenyl)cyclohex-2-en-1-one (0.40 g, 1.10 mmole) in ethanol (50 ml). The mixture was evaporated to dryness and the residue dissolved in acetone (50 ml). 4-Toluenesulfonyl chloride (0.21 g, 1.10 mmole) was added and the mixture was stirred at room temperature for 2 hours, then evaporated to dryness under reduced pressure. The residue was purified by column chromatography over silica gel (eluant dichloromethane) to give 3-(4-toluenesulfonyl)oxy-2-[1-(ethoxyimino)-propyl]-5-(2-methoxy-3,4,5,6-tetramethylphenyl)cyclohex-2-en-1-one (0.59 g; 100%) as a yellow oil.

The product was characterized by proton nuclear magnetic resonance spectroscopy and spectroscopic data is recorded in Table 5, Example 20.

EXAMPLE 18

The 5-arylcyclohexane-1,3-diones of Formula IX used in the preparation of the compounds of formula I were prepared from the appropriate benzaldehyde derivative following essentially the same procedure as that described in Example 2 parts (i) and (ii).

The majority of the 5-arylcyclohexane-1,3-diones of formula IX were obtained as solids and were characterized by their nuclear magnetic resonance spectra. For convenience, proton nuclear magnetic resonance spectroscopic (pmr) data and/or melting point data is recorded in Table 3 below.

TABLE 3

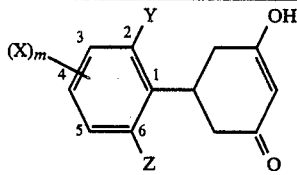

IX

| $(X)_m$ | Y | Z | Appearance | Proton Chemical Shift δ in ppm ($D_6$—DMSO) |
|---|---|---|---|---|
| 3-$CH_3O$—4-$CH_3$ | $CH_3$ | $CH_3$ | Colourless solid | 2.15(3H, s); 2.26(3H, s); 2.28(3H, s); 2.30–4.00 (5H, m); 3.58(3H, s); 5.32(1H, s); 6.83(1H, s); 11.2(1H, br.s). |
| 4-$CH_3$ | Cl | $CH_3$ | Yellow solid | 2.02–4.27(11H, m); 5.30 (1H, s); 7.09(1H, s); 7.20(1H, s); 11.6(1H, br.s). |
| 4-$CH_3$ | $CH_3$ | $CH_3O$ | Cream solid, mp 158° C. | Not recorded |
| 4-$CH_3$ | $CH_3O$ | $CH_3O$ | Yellow oil | 2.22(3H, s); 2.40–3.60 (4H, m); 3.80(6H, s); 3.90(1H, m); 5.20(1H, s); 6.20(2H, s); 11.0(1H, br.s). |
| 4-$CH_3$ | Br | Br | Yellow oil | 2.24(3H, s); 2.25–4.30(5H, m); 5.32(1H, s); 7.21(2H, s); 11.1(1H, br.s). |
| 4-Br | $CH_3$ | $CH_3$ | Yellow oil | 2.30(6H, s); 2.40–3.30(4H, m); 3.67(1H, s); 5.33(1H, s); 6.19(2H, s); 11.4(1H, br.s) |
| 3-$C_2H_5$—4-$CH_3$ | $CH_3$ | $CH_3$ | Pale yellow solid, mp 108° C. | Not recorded |
| 4-$CH_3$—3-n-$C_4H_9$ | $CH_3$ | $CH_3$ | Yellow oil | 0.95(3H, t); 2.40(4H, m); 2.20(3H, s); 2.27(6H, s); 2.30–4.00(7H, m); 5.40(1H, s); 6.80(1H, s); 11.0(1H, br.s) |
| 3-Cl—4-$CH_3$ | $CH_3$ | $CH_3$ | Yellow solid, mp 189° C. | Not recorded |
| 3-Br—4-$CH_3$ | $CH_3$ | $CH_3$ | Pale yellow solid, mp 136° C. | Not recorded |
| 3-F—4-$CH_3$ | $CH_3$ | $CH_3$ | Colourless solid, mp 128° C. | Not recorded |
| 3,4-$(CH_3)_2$ | $CH_3$ | $C_2H_5$ | Colourless solid | 1.10(3H, t); 2.10(3H, s); 2.20(3H, s); 2.24(3H, s); 2.30–3.95(6H, m); 3.80(1H, m); 5.53(1H, s); 6.80(1H, s); 11.0(1H, br.s). |
| 4-$C_2H_5$ | $C_2H_5$ | $C_2H_5$ | Colourless solid, mp 199° C. | Not recorded |
| 4-$CH_3$—$(CH_2)_3O$ | $CH_3$ | $CH_3$ | Cream solid, mp 160° C. | Not recorded |
| 4-$CH_3O$ | $CH_3O$ | $CH_3O$ | Yellow oil | 2.0–4.0(14H, m); 5.28(1H, s); 6.18(2H, s); 11.2(1H, br.s). |
| 3,4,5-$(CH_3)_3$ | $CH_3$ | $C_2H_5$ | Colourless solid, mp 200° C. | Not recorded |
| 3-$C_2H_5$—4,5-$(CH_3)_2$ | $CH_3$ | $CH_3$ | Colourless solid, mp 154° C. | Not recorded |
| 3,5-$(C_2H_5)_2$—4-$CH_3$ | $CH_3$ | $CH_3$ | Yellow oil | 1.00(6H, t); 2.10(3H, s); 2.17(6H, s); 2.20–4.00 (9H, m); 5.30(1H, s); 11.5(1H, br.s) |
| 3-Br—4,5-$(CH_3)_2$ | $CH_3$ | $CH_3$ | Cream solid, mp 248° C. | Not recorded |
| 3,5-$(CH_3)_2$—4-$C_2H_5$ | $CH_3$ | $CH_3$ | Colourless solid, mp 198° C. | Not recorded |

TABLE 3-continued

IX: Structure — benzene ring with (X)$_m$ substituents at positions 3,4,5; Y at position 2; Z at position 6; position 1 attached to a cyclohexane ring bearing OH and =O (5-aryl-cyclohexane-1,3-dione tautomer).

| (X)$_m$ | Y | Z | Appearance | Proton Chemical Shift δ in ppm (D$_6$—DMSO) |
|---|---|---|---|---|
| 3-Br—4,5-(CH$_3$)$_2$ | C$_2$H$_5$ | CH$_3$ | Yellow oil | 1.01(3H, t); 2.10(3H, s); 2.20(3H, s); 2.40(3H, s); 2.40–4.07(7H, m); 5.24 (1H, s); 11.2(1H, br.s). |
| 4-Br—3,5-(CH$_3$)$_2$ | CH$_3$ | CH$_3$ | Cream solid, mp >250° C. | Not recorded |
| 3,5-Cl$_2$—4-CH$_3$ | CH$_3$ | CH$_3$ | Colourless solid, mp 220° C. | Not recorded |
| 3-Cl—4-CH$_3$ | CH$_3$ | OCH$_3$ | Colourless solid, mp 200° C. | Not recorded |
| 3,4,5-(CH$_3$)$_3$ | Br | CH$_3$ | Colourless solid, mp >250° C. | Not recorded |
| 3-F—4,-5-(CH$_3$)$_2$ | CH$_3$ | CH$_3$ | Cream solid, mp 220° C. | Not recorded |
| 4-CH$_3$ | OC$_2$H$_5$ | CH$_3$ | Cream solid, mp 193° C. | Not recorded |
| 3-Cl—4,5-(CH$_3$)$_2$ | CH$_3$ | CH$_3$ | Yellow oil | 2.17(3H, s); 2.23(3H, s); 2.31(3H, s); 2.42(3H, s); 3.65–4.15(5H, m); 5.34(1H, s); 11.0(1H, br.s) |
| 3-Cl—4,5-(CH$_3$)$_2$ | CH$_3$ | OCH$_3$ | Colourless solid, mp 182° C. | Not recorded |
| 3,4-(CH$_3$)$_2$ | OCH$_3$ | CH$_3$ | Colourless solid, mp 204° C. | Not recorded |
| 3,4,5-(CH$_3$)$_3$ | Cl | CH$_3$ | Colourless solid, mp 218–222° C. | Not recorded |
| 3,4-(CH$_3$)$_2$ | CH$_3$ | OCH$_3$ | Colourless solid, mp 215° C. | Not recorded |
| 3,5-(CH$_3$)$_2$—4-OCH$_3$ | CH$_3$ | CH$_3$ | Cream solid, mp 166° C. | Not recorded |
| 4-CH$_3$ | Br | CH$_3$ | Yellow oil | 2.02–2.36(9H, m); 2.82–3.57(2H, m); 5.30(1H, s); 7.03(1H, s); 7.29(1H, s); 11.2(1H, br.s) |
| 3,4,5-(CH$_3$)$_3$ | OCH$_3$ | CH$_3$ | Colourless solid, mp 219° C. | Not recorded |
| 3,4,5-(CH$_3$)$_3$ | F | CH$_3$ | Colourless solid, mp 212–216° C. | Not recorded |
| 3,4-(CH$_3$)$_2$ | CH$_3$ | F | Colourless solid, mp 220° C. | Not recorded |
| 3-OCH$_3$—4,5-(CH$_3$)$_2$ | CH$_3$ | CH$_3$ | Colourless solid, mp 178° C. | Not recorded |
| 3,4-(CH$_3$)$_2$ | CH$_3$ | Cl | Colourless solid, mp 230° C. | Not recorded |
| 3,4-(CH$_3$)$_2$ | CH$_3$ | Br | Colourless solid, mp 217° C. | Not recorded |
| 3,4-(CH$_3$)$_2$—5-Br | CH$_3$ | H | Yellow solid, mp 210° C. | Not recorded |
| 3,4,5-(CH$_3$)$_3$ | OCH$_3$ | H | Pale cream solid, mp 210–215° C. | Not recorded |
| 4-Cl | Cl | Cl | Yellow oil | 2.0–3.4(4H, m); 4.40(1H, m); 5.35(1H, s); 7.60(1H, s); 12.0(1H, br.s). |

EXAMPLE 19

The 2-acyl-5-arylcyclohexane-1,3-diones of formula XIII used in the preparation of the compounds of formula I were prepared from the corresponding 5-arylcyclohexane-1,3-dione of formula IX by acylation using the appropriate acyl derivative following essentially the same procedure as that described in Example 2 part (iii).

The majority of the 2-acyl-5-arylcyclohexane-1,3-diones of formula XIII were obtained as oils and were characterized by their nuclear magnetic resonance spectra. For convenience, proton nuclear magnetic resonance spectroscopic (pmr) data and/or melting point data is recorded in Table 4 below.

TABLE 4

(XIII)

| $(X)_m$ | Y | Z | $R^3$ | Appearance | Proton Chemical Shift δ in ppm (CDCl$_3$) |
|---|---|---|---|---|---|
| 3-OCH$_3$—4-CH$_3$ | CH$_3$ | CH$_3$ | C$_2$H$_5$ | Pale yellow oil | 1.15(3H, t); 2.23(3H, s); 2.33(6H, s); 2.35–4.00(7H, m); 3.66(3H, s); 6.84(1H, s); 18.24(1H, s). |
| 4-CH$_3$ | Cl | CH$_3$ | C$_2$H$_5$ | Yellow oil | 1.18(3H, t); 2.28(3H, s); 2.36(3H, s); 2.40–4.00(7H, m); 6.96(1H, s); 7.09(1H, s); 18.34(1H, s). |
| 4-CH$_3$ | CH$_3$ | CH$_3$O | C$_2$H$_5$ | Yellow oil | 1.12(3H, t); 2.13–2.74(5H, m); 2.28 (3H, s); 3.11(2H, q); 3.26–3.75(3H, m); 3.80(3H, s); 6.63(2H, s); 18.30(1H, s). |
| 4-CH$_3$ | CH$_3$O | CH$_3$O | C$_2$H$_5$ | Yellow oil | 1.10(3H, t); 2.30(3H, s); 2.30–3.60 (6H, m); 3.80(6H, s); 3.90(1H, m); 6.40(2H, s); 18.20(1H, s). |
| 4-CH$_3$ | Br | Br | C$_2$H$_5$ | Yellow solid, mp 128° C. | Not recorded |
| 4-Br | CH$_3$ | CH$_3$ | C$_2$H$_5$ | Brown oil | 1.15(3H, t); 2.37(6H, s); 2.50–3.30 (6H, m); 3.65(1H, m); 7.15(2H, s); 18.20(1H, s). |
| 3-C$_2$H$_5$—4-CH$_3$ | CH$_3$ | CH$_3$ | C$_2$H$_5$ | Brown oil | 1.00–1.25(6H, m); 2.27(3H, s); 2.32 (6H, s); 2.35–3.40(8H, m); 3.81(1H, m); 6.80(1H, s); 18.20(1H, s). |
| 4-CH$_3$ 3-n-C$_4$H$_9$ | CH$_3$ | CH$_3$ | C$_2$H$_5$ | Brown oil | 0.95(3H, t); 1.18(3H, t); 1.40(4H, m); 2.10(3H, s); 2.15(6H, s); 2.45–3.40(8H, m); 3.90(1H, m); 6.80(1H, s); 18.20(1H, s). |
| 3-Cl—4-CH$_3$ | CH$_3$ | CH$_3$ | C$_2$H$_5$ | Yellow oil | 1.16(3H, t); 2.32(3H, s); 2.34(3H, s); 2.46(3H, s); 2.47–4.40(7H, m); 6.92(1H, s); 18.26(1H, s). |
| 3-Br—4-CH$_3$ | CH$_3$ | CH$_3$ | C$_2$H$_5$ | Yellow oil | 1.15(3H, t); 2.30(6H, s); 2.50(3H, s); 2.52–3.60(6H, m); 3.95(1H, m); 6.90(1H, s); 18.20(1H, s). |
| 3-F—4-CH$_3$ | CH$_3$ | CH$_3$ | C$_2$H$_5$ | Yellow oil | 1.18(3H, t); 2.20(3H, d); 2.30(6H, m); 2.32–3.30(6H, m); 6.80(1H, d); 18.20(1H, s). |
| 3,4-(CH$_3$)$_2$ | CH$_3$ | C$_2$H$_5$ | C$_2$H$_5$ | Yellow oil | 1.10(6H, t); 2.10(3H, s); 2.20(3H, s); 2.24(3H, s); 2.30–3.40(8H, m); 3.80(1H, m); 6.85(1H, s); 18.20(1H, s). |
| 4-C$_2$H$_5$ | C$_2$H$_5$ | C$_2$H$_5$ | C$_2$H$_5$ | Yellow oil | 1.00–1.20(12H, m); 2.15–3.00(10H, m); 2.35(2H, q); 3.70(1H, m); 6.90(2H, 3); 18.10(1H, s). |
| 4-Cl | Cl | Cl | C$_2$H$_5$ | Yellow oil | 1.10(3H, t); 2.20–3.80(6H, m); 4.20 (1H, m); 7.50(2H, s); 18.20(1H, s). |
| 4-CH$_3$ | Cl | CH$_3$ | n-C$_3$H$_7$ | Brown oil | 1.00(3H, t); 1.65(2H, m); 2.26(3H, s); 2.34(3H, s); 2.74–4.00(7H, m); 6.88(1H, s); 7.02(1H, s); 18.29(1H, s). |
| 4-CH$_3$—(CH$_2$)$_3$O | CH$_3$ | CH$_3$ | C$_2$H$_5$ | Yellow oil | 0.86–1.90(10H, m); 2.36(6H, s); 2.51–3.80(7H, m); 3.92(2H, t); 6.57(2H, s); 18.33(1H, s). |
| 4-OCH$_3$ | OCH$_3$ | OCH$_3$ | C$_2$H$_5$ | Yellow oil | 1.10(3H, t); 2.20–4.00(16H, m); 6.10 (2H, s); 18.00(1H, s). |
| 3,4,5-(CH$_3$)$_3$ | CH$_3$ | C$_2$H$_5$ | C$_2$H$_5$ | Orange oil | 1.00–1.30(6H, m); 2.18–2.25(12H, m); 2.25–3.40(8H, m); 3.80(1H, m); 18.20(1H, s). |
| 3-C$_2$H$_5$—4,5-(CH$_3$)$_2$ | CH$_3$ | CH$_3$ | C$_2$H$_5$ | Yellow oil | 1.00–1.27(6H, m); 2.19–2.27(12H, m); 2.28–3.41(8H, m); 4.00(1H, m); 18.20(1H, s). |
| 3,5-(C$_2$H$_5$)$_2$—4-CH$_3$ | CH$_3$ | CH$_3$ | C$_2$H$_5$ | Orange oil | 1.00–1.20(9H, m); 2.15(3H, s); 2.18 (6H, s); 2.20–3.40(10H, m); 3.80(1H, m); 18.20(1H, s). |
| 3-Br—4,5-(CH$_3$)$_2$ | CH$_3$ | CH$_3$ | C$_2$H$_5$ | Yellow oil | 1.18(3H, t); 2.30(6H, s); 2.47(3H, s); 2.54(3H, s); 2.64–4.19(7H, m); 18.34(1H, s). |
| 3,5-(CH$_3$)$_2$—4-C$_2$H$_5$ | CH$_3$ | CH$_3$ | C$_2$H$_5$ | Orange oil | 1.00–1.20(6H, m); 2.10(6H, s); 2.12 (6H, s); 2.40–3.40(8H, m); 4.00(1H, m); 18.20(1H, s). |
| 3-Br—4,5-(CH$_3$)$_2$ | C$_2$H$_5$ | CH$_3$ | C$_2$H$_5$ | Yellow oil | 1.10(6H, t); 2.20(3H, s); 2.25(3H, s); 2.40(3H, s); 2.40–3.40(8H, m); 3.98(1H, m); 18.20(1H, s). |
| 4-Br—3,5-(CH$_3$)$_2$ | CH$_3$ | CH$_3$ | C$_2$H$_5$ | Yellow oil | 1.18(3H, t); 2.35(6H, s); 2.46(6H, s); 2.61–4.16(7H, m; 18.34(1H, s). |
| 4-CH$_3$ | OCH$_3$ | CH$_3$ | n-C$_3$H$_7$ | Yellow oil | 1.01(3H, t); 1.70(2H, m); 2.30(6H, s); 2.42–2.65(2H, m); 3.05(2H, t); |

TABLE 4-continued

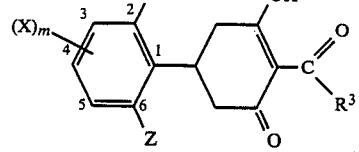
(XIII)

| (X)$_m$ | Y | Z | R$^3$ | Appearance | Proton Chemical Shift δ in ppm (CDCl$_3$) |
|---|---|---|---|---|---|
| 3,5-Cl$_2$—4-CH$_3$ | CH$_3$ | CH$_3$ | C$_2$H$_5$ | Yellow oil, slowly solidified | 3.30–3.74(3H, m); 3.86(3H, s); 6.62 (2H, s); 18.32(1H, s). 1.15(3H, t); 2.00–4.29(7H, m); 2.47 (9H, s); 18.28(1H, s). |
| 3-Cl—4-CH$_3$ | CH$_3$ | CH$_3$ | n-C$_3$H$_7$ | Yellow oil | 1.00(3H, t); 1.68(2H, m); 2.33(6H, s); 2.45(3H, s); 2.45–4.40(7H, m); 6.94(1H, s); 18.20(1H, s). |
| 3-Cl—4-CH$_3$ | CH$_3$ | OCH$_3$ | C$_2$H$_5$ | Colourless solid, mp 158° C. | Not recorded |
| 3,4,5-(CH$_3$)$_3$ | Br | CH$_3$ | C$_2$H$_5$ | Yellow oil | 1.18(3H, t); 2.21(3H, s); 2.30(3H, s); 2.35(3H, s); 2.45(3H, s); 2.53– 4.36(5H, m); 3.13(2H, q); 18.34(1H, s). |
| 3-F—4,-5-(CH$_3$)$_2$ | CH$_3$ | CH$_3$ | C$_2$H$_5$ | Yellow oil | 1.18(3H, t); 2.18(6H, s); 2.30(6H, s); 2.41–4.10(7H, m); 18.32(1H, s). |
| 3-F—4,-5-(CH$_3$)$_2$ | CH$_3$ | CH$_3$ | n-C$_3$H$_7$ | Yellow oil | 1.00(3H, t); 1.69(2H, m); 2.18(6H, s); 2.30(6H, s); 2.44–4.07(7H, m); 18.37(1H, s). |
| 3,5-(CH$_3$)$_2$—4-C$_2$H$_5$ | CH$_3$ | CH$_3$ | n-C$_3$H$_7$ | Yellow oil | 1.00–1.20(6H, m); 1.70(2H, m); 2.10 (6H, s); 2.15(6H, s); 2.20–3.40(8H, m); 3.90(1H, m); 18.20(1H, s). |
| 4-CH$_3$ | OC$_2$H$_5$ | CH$_3$ | C$_2$H$_5$ | Yellow oil | 1.18(3H, t); 1.41(3H, t); 2.28(6H, s); 2.36–2.65(2H, m); 3.11(2H, q); 3.28–3.80(3H, m); 4.03(2H, q); 6.60(2H, s); 18.33(1H, s). |
| 3-F—4-CH$_3$ | CH$_3$ | CH$_3$ | n-C$_3$H$_7$ | Yellow oil | 1.00(3H, t); 1.69(2H, m); 2.21–2.32 (9H, m); 2.44–3.90(7H, m); 6.86(1H, d); 18.39(1H, s). |
| 3-Cl—4,5-(CH$_3$)$_2$ | CH$_3$ | CH$_3$ | C$_2$H$_5$ | Yellow oil | 1.18(3H, t); 2.22(3H, s); 2.31(3H, s); 2.37(3H, s); 2.47(3H, s); 2.62 (1H, d); 2.75(1H, d); 2.88–3.30(4H, m); 3.68–4.15(1H, m); 18.20(1H, s). |
| 3-Cl—4,5-(CH$_3$)$_2$ | CH$_3$ | CH$_3$ | n-C$_3$H$_7$ | Pale yellow solid, mp <50° C. | 1.15(3H, t); 1.68(2H, m); 2.23(3H, s); 2.30(3H, s); 2.38(3H, s); 2.47 (3H, s); 2.60(1H, d); 2.75(1H, d); 2.85–3.20(4H, m); 3.65–4.15(1H, m); 18.25(1H, s). |
| 3-Cl—4,5-(CH$_3$)$_2$ | CH$_3$ | OCH$_3$ | C$_2$H$_5$ | Colourless solid, mp 96° C. | Not recorded |
| 3,4-(CH$_3$)$_2$ | OCH$_3$ | CH$_3$ | n-C$_3$H$_7$ | Yellow oil | 1.00(3H, t); 1.69(2H, m); 2.18(3H, s); 2.22(3H, s); 2.30(3H, s); 2.50– 3.80(7H, m); 3.72(3H, s); 6.80(1H, s); 18.39(1H, s). |
| 3,4,5-(CH$_3$)$_3$ | Cl | CH$_3$ | n-C$_3$H$_7$ | Yellow oil | 1.01(3H, s); 1.68(2H, m); 2.22(3H, s); 2.26(3H, s); 2.31(3H, s); 2.36 (3H, s); 2.40–4.40(7H, m); 18.33(1H, s). |
| 3,4-(CH$_3$)$_2$ | OCH$_3$ | CH$_3$ | C$_2$H$_5$ | Yellow oil | 1.18(3H, t); 2.25(9H, m); 2.47–3.72 (5H, m); 3.10(2H, q); 3.72(3H, s); 6.78(1H, s); 18.28(1H, s). |
| 3-Br—4,5-(CH$_3$)$_2$ | CH$_3$ | CH$_3$ | n-C$_3$H$_7$ | Yellow oil | 1.02(3H, t); 1.69(2H, m); 2.30(6H, s); 2.47(3H, s); 2.54(3H, s); 2.63– 4.19(7H, m); 18.41(1H, s). |
| 3,4-(CH$_3$)$_2$ | CH$_3$ | OCH$_3$ | n-C$_3$H$_7$ | Yellow oil | 1.00(3H, t); 1.69(2H, m); 2.17(3H, 2.24(3H, s); 2.30(3H, s); 2.50–3.80 (7H, m); 3.79(3H, s); 6.65(1H, s); 18.37(1H, s). |
| 3,5-Cl$_2$—4-CH$_3$ | CH$_3$ | CH$_3$ | n-C$_3$H$_7$ | Yellow oil | 1.08(3H, t); 1.42–4.15(9H, m); 2.46 (9H, s); 18.34(1H, s). |
| 3-OCH$_3$—4-CH$_3$ | CH$_3$ | CH$_3$ | n-C$_3$H$_7$ | Yellow oil | 1.00(3H, t); 1.68(2H, m); 2.20(3H, s); 2.28(6H, s); 2.60–3.92(7H, m); 3.64(3H, s); 6.80(1H, s); 18.24(1H, s). |
| 3,4-(CH$_3$)$_2$ | CH$_3$ | OCH$_3$ | C$_2$H$_5$ | Yellow oil | 1.18(3H, t); 2.17(3H, s); 2.25(3H, s); 2.30(3H, s); 2.50–3.80(7H, m); 3.79(3H, s); 6.65(1H, s); 18.30(1H, s). |
| 3,5-(CH$_3$)$_2$—4-OCH$_3$ | CH$_3$ | CH$_3$ | n-C$_3$H$_7$ | Cream solid, mp 112° C. | Not recorded |
| 3,4,5-(CH$_3$)$_3$ | Br | CH$_3$ | n-C$_3$H$_7$ | Brown oil | 1.00(3H, t); 1.69(2H, m); 2.22(3H, s); 2.29(3H, s); 2.34(3H, s); 2.43 (3H, s); 2.00–4.90(7H, m); 18.33(1H, s). |
| 3,4,5-(CH$_3$)$_3$ | Cl | CH$_3$ | C$_2$H$_5$ | Yellow oil | 1.16(3H, t); 2.21(3H, s); 2.25(3H, s); 2.32(3H, s); 2.35(3H, s); 2.40– 4.40(7H, m); 18.31(1H, s). |
| 4-CH$_3$ | Br | CH$_3$ | n-C$_3$H$_7$ | Yellow oil | 1.18(3H, t); 1.41(3H, t); 2.28(6H, |

TABLE 4-continued (XIII) structure: cyclohexenone with OH, C(=O)R³, substituted phenyl bearing (X)ₘ at positions 3,4,5 and Y at 2, Z at 6.

| (X)ₘ | Y | Z | R³ | Appearance | Proton Chemical Shift δ in ppm (CDCl₃) |
|---|---|---|---|---|---|
| | | | | | s); 2.36–2.65(2H, m); 3.11(2H, q); 3.28–3.80(3H, m); 4.03(2H, q); 6.60 (2H, s); 18.33(1H, s). |
| 3,4,5-(CH₃)₃ | OCH₃ | CH₃ | n-C₃H₇ | Yellow oil | 1.00(3H, t); 1.69(2H, m); 2.21(9H, s); 2.27(3H, s); 2.44–3.50(7H, m); 3.68(3H, s); 18.39(1H, s). |
| 3,4,5-(CH₃)₃ | F | CH₃ | n-C₃H₇ | Pale yellow solid, mp 105° C. | Not recorded |
| 3,4-(CH₃)₂ | CH₃ | F | n-C₃H₇ | Pale yellow solid, mp 96–98° C. | Not recorded |
| 3-(OCH₃)—4,5-(CH₃)₂ | CH₃ | CH₃ | n-C₃H₇ | Yellow oil | 1.00(3H, t); 1.68(2H, m); 2.16(3H, s); 2.20(3H, s); 2.24(3H, s); 2.28 (3H, s); 2.44–3.20(6H, m); 3.72(3H, s); 3.75–4.08(1H, m); 18.28(1H, s). |
| 3,4-(CH₃)₂ | CH₃ | Cl | n-C₃H₇ | Pale yellow solid, mp 97–99° C. | Not recorded |
| 3,4-(CH₃)₂ | CH₃ | Br | n-C₃H₇ | Colourless oil | 0.98(3H, t); 1.70(2H, m); 2.14(3H, s); 2.23(3H, s); 2.32(3H, s); 2.00–4.40(7H, m); 7.26(1H, s); 18.31(1H, s). |
| 3,4,5-(CH₃)₃ | OCH₃ | CH₃ | C₂H₅ | Colourless oil | 1.15(3H, t); 2.17(9H, s); 2.23(3H, s); 2.34–4.00(7H, m); 3.66(3H, s); 18.17(1H, s). |
| 3,4-(CH₃)₂—5-Br | CH₃ | H | n-C₃H₇ | Yellow oil | 1.00(3H, t); 1.70(2H, m); 2.20(6H, s); 2.40(3H, s); 2.50–3.10(6H, m); 3.80(1H, m); 6.80(1H, s); 18.20(1H, s). |
| 3,4,5-(CH₃)₃ | OCH₃ | H | n-C₃H₇ | Colourless oil | 1.00(3H, t); 1.69(2H, m); 2.14(3H, s); 2.22(3H, s); 2.23(3H, s); 2.50–3.15(7H, m); 3.64(3H, s); 6.78(1H, s); 18.21(1H, s). |

EXAMPLE 20

The majority of the compounds of the invention were obtained as oils and were characterized by, and can be identified by their nuclear magnetic resonance spectra. For convenience proton nuclear magnetic resonance spectroscopic (pmr) data and/or melting point data is recorded in Table 5 below.

TABLE 5

| Compound No | Appearance | Proton Chemical Shift δ in ppm (CDCl₃) |
|---|---|---|
| 1 | Pale yellow oil, solidified slowly | 1.20(3H,t); 1.32(3H,t); 2.23 (3H,s); 2.34(6H,s); 2.35–4.00 (7H,m); 3.65(3H,s); 4.12(2H,q); 6.83(1H,s); 14.95(1H,s). |
| 2 | Yellow oil | 1.09–1.41(6H,m); 2.25(3H,s); 2.36(3H,s); 2.45–4.00(7H,m); 4.21(2H,q); 6.90(1H,s); 7.03 (1H,s); 15.00(1H,s). |
| 3 | Pale yellow oil | 1.21(3H,t); 2.25(3H,s); 2.35 (3H,s); 2.50–4.00(7H,m); 4.55 (2H,d); 5.26–5.45(2H,m); 5.79–6.15(1H,m); 6.90(1H,s); 7.03 (1H,s); 14.02(1H,s). |
| 4 | Yellow oil | 1.11–1.42(6H,m); 2.25(6H,s); 2.93(2H,q); 3.13–3.64(5H,m); 3.76(3H,s); 4.10(2H,q); 6.58 (2H,s); 14.75(1H,s). |
| 5 | Oil | 1.10–1.40(6H,m); 2.32(3H,s); 2.35–3.75(7H,m); 3.76(6H,s); 4.10(2H,q); 6.37(2H,s); 15.00 (1H,s). |
| 6 | Yellow oil | 1.11–1.41(6H,m); 2.27(3H,s); 2.47(2H,m); 2.94(2H,q); 4.00–4.37(5H,m); 7.39(2H,s); 15.00 (1H,s). |
| 7 | Yellow solid, mp 131° C. | 1.10–1.41(6H,m); 2.38(6H,s); 2.63–3.09(6H,m); 3.78(1H,m); 4.12(2H,q); 7.16(2H,s); 15.12 (1H,s). |
| 8 | Yellow oil | 1.02–1.40(9H,m); 2.27(3H,s); 2.36(6H,s); 2.47–2.99(8H,m); 4.00–4.23(3H,m); 6.84(1H,s); 14.95(1H,s). |
| 9 | Yellow oil | 1.02–1.29(6H,m); 2.26(3H,s); 2.35(6H,s); 2.35–2.99(8H,m); 3.90(1H,m); 4.53(2H,d); 5.23–5.44(2H,m); 5.84(1H,m); 6.83 (1H,s); 14.54(1H,s). |
| 10 | Yellow oil | 0.97–1.41(13H,m); 2.27(3H,s); 2.35(6H,s); 2.35–2.99(8H,m); 4.00–4.24(3H,m); 6.85(1H,s); 14.99(1H,s). |
| 11 | Yellow oil | 1.11–1.41(6H,m); 2.31(3H,s); 2.35(3H,s); 2.47(3H,s); 2.47–3.14(6H,m); 3.87(1H,m); 4.12 (2H,q); 6.91(1H,s); 15.06 (1H,s). |
| 12 | Yellow oil | 1.11–1.41(6H,m); 2.34(6H,s); 2.53(3H,s); 2.59–3.12(6H,m); 3.73–4.24(3H,m); 6.91(1H,s); 15.05(1H,s). |
| 13 | Yellow oil | 1.20(3H,t); 2.33(3H,s); 2.36 (3H,s); 2.53(3H,s); 2.57–2.98 (6H,m); 3.88(1H,m); 4.54(2H,d); |

TABLE 5-continued

| Compound No | Appearance | Proton Chemical Shift δ in ppm (CDCl₃) |
|---|---|---|
| 14 | Yellow oil | 5.29–5.46(2H,m); 5.85(1H,m); 6.92(1H,s); 14.65(1H,s). |
| 15 | Yellow oil | 1.11–1.41(6H,m); 2.17(3H,d); 2.31(6H,s&d); 2.39–3.13(6H,m); 3.80–4.24(3H,m); 6.80(1H,d); 15.02(1H,s). |
| | | 1.11–1.40(9H,m); 2.15(3H,s); 2.25(3H,s); 2.33(3H,s); 2.35–2.98(8H,m); 4.07–4.16(3H,m); 6.88(1H,s); 14.97(1H,s). |
| 16 | Yellow/orange oil | 1.14–1.41(15H,m); 2.27–3.07(12H,m); 3.75(1H,m); 4.12(2H,q); 6.89(2H,s); 14.98(1H,s). |
| 17 | Yellow oil | 1.03–1.33(15H,m); 2.16–3.90(12H,m); 3.91–4.09(3H,m); 6.89(2H,s); 7.25–8.07(5H,m). |
| 18 | Yellow oil | 1.11–1.42(6H,m); 2.48(2H,m); 2.96(2H,m); 3.56(2H,t); 4.01–4.33(3H,m); 7.34(2H,s); 15.16(1H,s). |
| 19 | Yellow oil | 0.93(3H,m); 1.26(3H,t); 1.57(2H,m); 2.26(3H,s); 2.37(3H,s); 2.50–3.85(7H,m); 4.22(2H,q); 6.92(1H,s); 7.05(1H,s); 15.16(1H,s). |
| 20 | Yellow oil | 0.93(3H,t); 1.23(3H,t); 1.39(2H,m); 2.15(3H,s); 2.24(3H,s); 2.35(3H,s); 2.40–4.30(9H,m); 6.89(1H,s); 6.99(1H,s). |
| 21 | Yellow oil | 0.90–1.74(13H,m); 2.38(6H,s); 2.59–3.33(6H,m); 3.77–4.24(5H,m); 6.56(2H,s); 15.01(1H,s). |
| 22 | Pale yellow solid, mp 139° C. | 0.95–1.26(6H,m); 2.03–2.70(4H,m); 3.08–4.12(14H,m); 6.13(2H,s); 7.44–8.07(5H,m). |
| 23 | Pale yellow solid, mp 89° C. | 1.18–1.39(6H,m); 2.47–2.98(6H,m); 3.79(9H,s); 4.10(3H,m); 6.13(2H,s); 14.70(1H,s). |
| 24 | Yellow oil | 1.06–1.41(9H,m); 2.20(3H,s); 2.23(3H,s); 2.27(3H,s); 2.35(3H,s); 2.70–3.07(8H,m); 4.01–4.25(3H,m); 14.95(1H,s). |
| 25 | Yellow oil | 1.04–1.41(6H,m); 2.21(3H,s); 2.27(3H,s); 2.32(3H,s); 2.35(3H,s); 2.36–3.05(8H,m); 4.00–4.17(3H,m); 15.05(1H,s). |
| 26 | Yellow oil | 1.05–1.41(12H,m); 2.30(3H,s); 2.36(6H,s); 2.36–2.99(10H,m); 4.00–4.24(3H,m); 14.95(1H,s). |
| 27 | Pale yellow solid, mp 125° C. | 1.12–1.41(6H,m); 2.26(3H,s); 2.30(3H,s); 2.46(3H,s); 2.54(3H,s); 2.61–3.96(7H,m); 4.13(2H,q); 15.00(1H,s). |
| 28 | Yellow oil | 1.04–1.41(9H,m); 2.23(6H,s); 2.31(6H,s); 2.45–3.07(8H,m); 3.86–4.24(3H,m); 14.93(1H,s). |
| 29 | Yellow oil | 1.12–1.41(9H,m); 2.24(3H,s); 2.32(3H,s); 2.45(3H,s); 2.82–3.02(8H,m); 4.01–4.25(3H,m); 15.04(1H,s). |
| 30 | Yellow oil | 1.00(3H,t); 1.61(2H,m); 2.30(6H,s); 2.45–4.00(7H,m); 3.79(3H,s); 4.54(2H,d); 5.17–5.46(2H,m); 5.80–6.21(1H,m); 6.61(2H,s); 14.68(1H,s). |
| 31 | Yellow oil | 1.12–1.41(6H,m); 2.36(6H,s); 2.44(6H,s); 2.58–3.96(7H,m); 4.13(2H,q); 15.05(1H,s). |
| 32 | Pale yellow oil | 1.00(3H,t); 1.31(3H,t); 1.63(2H,m); 2.28(6H,s); 2.46(2H,m); 2.94(2H,t); 3.56(3H,m); 3.78(3H,s); 4.10(2H,q); 6.59(2H,s); 14.93(1H,s). |
| 33 | Pale yellow oil | 1.20(3H,t); 1.34(3H,t); 2.23–3.43(6H,m); 2.47(9H,s); 3.71–4.31(3H,m); 15.10(1H,s). |
| 34 | Yellow oil | 1.20(3H,t); 2.32(3H,s); 2.34(3H,s); 2.47(3H,s); 2.48–4.10(7H,m); 4.51(2H,d); 4.59–5.39(2H,m); 5.97–6.16(1H,m); 6.92(1H,s); 14.65(1H,s). |
| 35 | Yellow oil | 1.20(3H,t); 2.32(3H,s); 2.35(3H,s); 2.47(3H,s); 2.47–3.22(6H,m); 3.42–3.72(1H,m); 4.02–4.21(1H,m); 4.38–4.53(2H,m); 4.90–4.99(1H,m); 6.92(1H,s); 14.10(1H,s). |
| 36 | Yellow oil | 1.00(3H,t); 1.33(3H,t); 1.59(2H,m); 2.32(3H,s); 2.34(3H,s); 2.47(3H,s); 2.50–4.00(7H,m); 4.12(2H,q); 6.92(1H,s); 15.18(1H,s). |
| 37 | Yellow oil | 1.00(3H,t); 1.59(2H,m); 2.32(3H,s); 2.34(3H,s); 2.47(3H,s); 2.48–4.10(7H,m); 4.51(2H,d); 4.59–5.39(2H,m); 5.97–6.16(1H,m); 6.92(1H,s); 14.72(1H,s). |
| 38 | Yellow oil | 0.99(3H,t); 1.58(2H,m); 2.32(3H,s); 2.34(3H,s); 2.47(3H,s); 2.50–4.00(7H,m); 4.15(1H,m); 4.43(2H,m); 4.95(1H,m); 6.92(1H,s); 14.15(1H,s). |
| 39 | Colourless solid, mp 145° C. | 1.16(3H,t); 1.32(3H,t); 2.37(3H,s); 2.42(3H,s); 2.90–3.75(7H,m); 3.79(3H,s); 4.08(2H,q); 6.60(1H,s); 14.94(1H,s). |
| 40 | Yellow oil | 1.12–1.41(6H,m); 2.20(3H,s); 2.28(3H,s); 2.35(3H,s); 2.44(3H,s); 2.60–4.00(7H,m); 4.09(2H,q); 15.00(1H,s). |
| 41 | Yellow oil | 1.12–1.41(6H,m); 2.17(6H,s); 2.27(6H,s); 2.41–3.99(7H,m); 4.13(2H,q); 15.00(1H,s). |
| 42 | Yellow oil | 1.01(3H,t); 1.33(3H,t); 1.64(2H,m); 2.17(6H,s); 2.28(6H,s); 2.42–4.00(7H,m); 4.12(2H,q); 15.14(1H,s). |
| 43 | Yellow oil | 0.92–1.40(9H,m); 1.59(2H,m); 2.24(6H,s); 2.31(6H,s); 2.31–3.01(8H,m); 3.99–4.23(3H,m); 15.04(1H,s). |
| 44 | Orange oil | 1.11–1.49(9H,m); 2.28(6H,s); 2.49(2H,m); 2.41(2H,q); 3.57(3H,m); 4.07(4H,m); 6.59(2H,s); 14.84(1H,s). |
| 45 | Yellow oil | 1.01(3H,t); 1.33(3H,t); 1.61(2H,m); 2.21–2.32(9H,m); 2.58–4.00(7H,m); 4.12(2H,q); 6.86(1H,d); 15.17(1H,s). |
| 46 | Yellow solid, mp 106–107° C. | 1.12–1.41(6H,m); 2.22(3H,s); 2.31(3H,s); 2.37(3H,s); 2.47(3H,s); 2.60–3.36(6H,m); 3.85–4.24(3H,m); 15.02(1H,s). |
| 47 | Yellow solid, mp 108–109° C. | 1.01(3H,t); 1.33(3H,t); 1.42–1.80(2H,m); 2.23(3H,s); 2.30(3H,s); 2.38(3H,s); 2.47(3H,s); 2.52–3.55(6H,m); 3.60–4.25(3H,m); 15.13(1H,s). |
| 48 | Yellow oil | 1.20(3H,t); 1.33(3H,t); 2.23(3H,s); 2.33(3H,s); 2.43(3H,s); 2.52–3.92(7H,m); 3.68(3H,s); 4.13(2H,q); 15.00(1H,s). |
| 49 | Yellow oil | 1.01(3H,t); 1.32(3H,t); 1.64(2H,m); 2.17(3H,s); 2.21(3H,s); 2.31(3H,s); 2.41–3.56(7H,m); 3.70(3H,s); 4.12(2H,q); 6.76(1H,s); 15.05(1H,s). |
| 50 | Colourless solid, mp 132° C. | 1.00(3H,t); 1.32(3H,t); 1.58(2H,m); 2.21(3H,s); 2.25(3H,s); 2.32(3H,s); 2.36(3H,s); 2.50–4.00(7H,m); 4.11(2H,q); 15.07(1H,s). |
| 51 | Yellow oil | 1.11–1.40(6H,m); 2.17(3H,s); 2.21(3H,s); 2.30(3H,s); 2.47–3.57(7H,m); 3.70(3H,s); 4.12(2H,q); 6.76(1H,s); 14.95(1H,s). |

TABLE 5-continued

| Compound No | Appearance | Proton Chemical Shift δ in ppm (CDCl3) |
|---|---|---|
| 52 | Yellow oil | 1.01(3H,t); 1.33(3H,t); 1.64(2H,m); 2.26(3H,s); 2.30(3H,s); 2.45(3H,s); 2.54(3H,s); 2.63–4.00(7H,m); 4.12(2H,q); 15.13(1H,s). |
| 53 | Yellow oil | 1.00(3H,t); 1.32(3H,t) 1.62(2H,m); 2.15(3H,s); 2.25(3H,s); 2.28(3H,s); 2.47–3.80(7H,m); 3.78(3H,s); 4.11(2H,q); 6.60(1H,s); 14.98(1H,s). |
| 54 | Pale yellow oil, slowly solidifies | 1.00(3H,t); 1.33(3H,t); 1.43–3.43(8H,m); 2.47(9H,s); 3.72–4.29(1H,m); 4.11(2H,q); 15.03(1H,br.s). |
| 55 | Yellow oil | 1.00(3H,t); 1.33(3H,t); 1.61(2H,m); 2.24(3H,s); 2.34(6H,s); 2.60–3.36(6H,m); 3.67(3H,s); 3.67–3.92(1H,m); 4.12(2H,q); 6.84(1H,s); 15.13(1H,s). |
| 56 | Yellow oil | 1.11–1.40(6H,m); 2.15(3H,s); 2.25(3H,s); 2.28(3H,s); 2.47–3.80(7H,m); 3.78(3H,s); 4.11(2H,q); 6.60(1H,s); 14.83(1H,s). |
| 57 | Colourless solid, mp 122° C. | 1.00(3H,t); 1.32(3H,t); 1.60(2H,m); 2.21(6H,s); 2.28(6H,s); 2.48–3.24(6H,m); 3.64(3H,s); 3.76–3.90(1H,m); 4.12(2H,q); 15.07(1H,s). |
| 58 | Pale brown solid, mp 107° C. | 1.00(3H,t); 1.32(3H,t); 1.58(2H,m); 2.20(3H,s); 2.29(3H,s); 2.35(3H,s); 2.45(3H,s); 2.50–4.05(7H,m); 4.12(2H,q); 15.06(1H,s). |
| 59 | Colourless solid, mp 134° C. | 1.20(3H,t); 1.33(3H,t); 2.21(3H,s); 2.24(3H,s); 2.33(3H,s); 2.36(3H,s); 2.50–4.00(7H,m); 4.12(2H,q); 14.95(1H,s). |
| 60 | Yellow oil, solidified slowly | 1.00(3H,t); 1.32(3H,t); 1.61(2H,m); 2.24(3H,s); 2.38(3H,s); 2.54(2H,m); 2.94(2H,t); 3.10–4.06(3H,m); 4.12(2H,q); 6.93(1H,s); 7.26(1H,s); 15.16(1H,s). |
| 61 | Colourless solid, mp 260° C. | Not recorded |
| 62 | Yellow oil | 1.01(3H,t); 1.32(3H,t); 1.64(2H,m); 2.19(9H,s); 2.28(3H,s); 2.41–3.90(7H,m); 3.67(3H,s); 4.11(2H,q); 15.02(1H,s). |
| 63 | Colourless solid, mp >250° C. | Not recorded |
| 64 | Pale yellow solid, mp 105° C. | 1.00(3H,t); 1.32(3H,t); 1.58(2H,m); 2.19(9H,s); 2.25(3H,s); 2.30–3.95(7H,m); 4.11(2H,q); 15.09(1H,s). |
| 65 | Colourless solid, mp 121° C. | 1.00(3H,t); 1.32(3H,t); 1.57(2H,m); 2.16(3H,s); 2.26(6H,s); 2.30–3.80(7H,m); 4.11(2H,q); 6.72(1H,t); 15.18(1H,s). |
| 66 | Yellow oil | 1.01(3H,t); 1.33(3H,t); 1.59(2H,m); 2.18(3H,s); 2.24(3H,s); 2.30(3H,s); 2.33(3H,s); 2.20–3.32(6H,m); 3.64(3H,s); 3.64–3.94(1H,m); 4.12(2H,q); 15.11(1H,s). |
| 67 | Colourless oil | 1.00(3H,t); 1.32(3H,t); 1.58(2H,m); 2.17(3H,s); 2.24(3H,s); 2.31(3H,s); 2.50–4.10(7H,m); 4.17(2H,q); 7.05(1H,s); 15.15(1H,s). |
| 68 | Pale yellow oil | 1.00(3H,t); 1.32(3H,t); 1.68(2H,m); 2.14(3H,s); 2.22(3H,s); 2.33(3H,s); 2.50–4.15(7H,m); 4.17(2H,q); 7.26(1H,s); 15.07(1H,s). |
| 69 | Colourless solid, mp 240° C. | Not recorded |
| 70 | Pale yellow oil | 0.91(3H,t); 1.10(3H,t); 1.47(2H,m); 2.06–5.17(9H,m); 2.20(3H,s); 2.27(3H,s); 2.45(6H,s); 7.29–7.74(3H,m); 7.93–8.14(2H,m). |
| 71 | Green solid, mp 213° C. | Not recorded |
| 72 | Brown oil | 0.80–3.46(51H,m); 2.18(3H,s); 2.27(3H,s); 2.37(3H,s); 2.43(3H,s); 4.07(2H,s). |
| 73 | Pale yellow solid, mp 118–120° C. | 0.99(3H,t); 1.62(2H,m); 2.22(3H,s); 2.25(3H,s); 2.32(3H,s); 2.36(3H,s); 2.52(3H,t); 2.88(2H,t); 3.05–4.40(5H,m); 4.65(2H,d); 13.50(1H,s). |
| 74 | Colourless solid, mp 250° C. | Not recorded |
| 75 | Colourless solid, mp >265° C. | Not recorded |
| 76 | Cream solid, mp 114° C. | 1.20(3H,t); 1.33(3H,t); 2.21(9H,s); 2.28(3H,s); 2.40–3.90(7H,m); 3.68(3H,s); 4.12(2H,q); 14.93(1H,s). |
| 77 | Colourless solid, mp >250° C. | Not recorded |
| 78 | Yellow oil | 1.00(3H,t); 1.65(2H,m); 2.22(3H,s); 2.26(3H,s); 2.32(3H,s); 2.37(3H,s); 2.40–4.40(7H,m); 4.65(2H,s); 5.70(1H,d); 5.94(1H,d); 13.87(1H,s). |
| 79 | Colourless oil | 0.93(3H,t); 1.09(3H,t); 1.10–2.00(2H,m); 2.20(9H,s); 2.25–3.77(7H,m); 2.33(3H,s); 3.72(3H,s); 3.97(2H,q); 8.34(4H,m). |
| 80 | Colourless oil | 0.96(3H,t); 1.19(3H,t); 2.21(9H,s); 2.25–3.94(7H,m); 2.27(3H,s); 2.45(3H,s); 3.69(3H,s); 3.99(2H,q); 7.33(2H,d); 7.81(2H,d). |
| 81 | Yellow oil | 1.00(3H,t); 1.32(3H,t); 1.57(2H,m); 2.23(3H,s); 2.26(3H,s); 2.44(3H,s); 2.50–3.05(6H,m); 3.90(1H,m); 4.11(2H,q); 6.88(1H,s); 15.15(1H,s). |
| 82 | Colourless oil | 0.99(3H,t); 1.32(3H,t); 1.65(2H,m); 2.15(3H,s); 2.22(3H,s); 2.34(3H,s); 2.45–3.15(7H,m); 3.67(3H,s); 4.11(2H,q); 6.85(1H,s); 15.09(1H,s). |

EXAMPLE 21

This non-limiting Example illustrates the preparation of formulations of the compounds of the invention.

(a) Emulsifiable Concentrate

Compound No 4 was dissolved in toluene containing 7% v/v "Teric" N13 and 3% v/v "Kemmat" SC15B to give an emulsifiable concentrate which may be diluted with water to the required concentration to give an aqueous emulsion which may be applied by spraying.

("Teric" is a Trade Mark and "Teric" N13, is a product of ethoxylation of nonylphenyl; "Kemmat" is a Trade Mark and "Kemmat" SC15B is a formulation of calcium dodecylbenzenesulfonate.)

(b) Aqueous Suspension

Compound No 4 (5 parts by weight) and "Dyapol" PT (1 part by weight) was added to an aqueous solution (94 parts by weight) of "Teric" N8 and the mixture was ball milled to produce a stable aqueous suspension which may be diluted with water to the required concentration to give an aqueous suspension which may be applied by spraying. ("Dyapol" is a Trade Mark and "Dyapol" PT is an anionic suspending agent; "Teric" N8 is a product of ethoxylation of nonylphenol.)

(c) Emulsifiable Concentrate

Compound No 4 (10 parts by weight). "Teric" N13 (5 parts by weight) and "Kemmat" SC15B (5 parts by weight) were dissolved in "Solvesso" 150 (80 parts by weight) to give an emulsifiable concentrate which may be diluted with water to the required concentration to give an aqueous emulsion which may be applied by spraying. ("Solvesso" is a Trade Mark and "Solvesso" 150 is a high boiling point aromatic petroleum fraction).

(d) Dispersible Powder

Compound No 4 (10 parts by weight), "Matexil" DA/AC (3 parts by weight), "Aerosol" OT/B (1 part by weight) and china clay 298 (86 parts by weight) were blended and then milled to give a powder composition having a particle size below 50 microns. ("Matexil" is a Trade Mark and "Matexil" DA/AC is the disodium salt of a naphthalenesulfonic acid/formaldehyde condensate; "Aerosol" is a Trade Mark and "Aerosol" OT/B is a formulation of the dioctylester of sodium sulfosuccinic acid).

(e) High Strength Concentrate

Compound No 4 (99 parts by weight), silica aerogel (0.5 parts by weight) and synthetic amorphous silica (0.5 parts by weight) were blended and ground in a hammer-mill to produce a powder having a particle size less than 200 microns.

(f) Dusting Powder

Compound No 4 (10 parts by weight), attapulgite (10 parts by weight) and pyrophyllite (80 parts by weight) were thoroughly blended and then ground in a hammer-mill to produce a powder of particle size less than 200 microns.

Emulsifiable concentrates and/or suspensions of the compounds of the invention were prepared essentially as described in part (a), (b) or (c) above and then diluted with water, optionally containing a surface active agent and/or oil, to give aqueous compositions of the required concentration which were used, as described in Examples 22 and 23, in the evaluation of the pre-emergence and post-emergence herbicidal activity of the compounds.

EXAMPLE 22

The pre-emergent herbicidal activity of the compounds of the invention formulated as described in Example 21 was assessed by the following procedure:

The seeds of the test species were sown in rows 2 cm deep in soil contained in seed boxes. The monocotyledonous plants and the dicotyledonous plants were sown in separate boxes and after sowing the two boxes were sprayed with the required quantity of a composition of the invention. Two duplicate seed boxes were prepared in the same manner but were not sprayed with a composition of the invention and were used for comparison purposes. All the boxes were placed in a glasshouse, lightly watered with an overhead spray to initiate germination and then sub-irrigated as required for optimum plant growth. After three weeks the boxes were removed from the glasshouse and the effect of the treatment was visually assessed. The results are presented in Table 6 where the damage to plants is rated on a scale of from 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represents 100% kill. A dash (-) means that no experiment was carried out.

The names of the test plants are as follows:
Wh    Wheat
Ot    Wild Oats
Rg    Ryegrass
Jm    Japanese millet
P     Peas
Ip    Ipomea
Ms    Mustard
Sf    Sunflower

TABLE 6
PRE-EMERGENCE HERBICIDAL ACTIVITY

| Compound No | APPLICATION Rate (kg/ha) | Wh | Ot | Rg | Jm | P | Ip | Ms | Sf |
|---|---|---|---|---|---|---|---|---|---|
| 1 | 1.0 | 5 | 5 | 5 | 5 | 0 | 0 | 0 | 0 |
| 1 | 0.25 | 2 | 0 | 5 | 5 | 0 | 0 | 0 | 0 |
| 4 | 1.0 | 0 | 5 | 5 | 5 | 0 | 0 | 0 | 0 |
| 4 | 0.25 | 0 | 1 | 5 | 5 | 0 | 0 | 0 | 0 |
| 5 | 1.0 | 0 | 0 | 5 | 5 | 0 | 0 | 0 | 0 |
| 5 | 0.25 | 0 | 0 | 5 | 5 | 0 | 0 | 0 | 0 |
| 6 | 1.0 | 0 | 2 | 5 | 5 | 0 | 0 | 0 | 0 |
| 6 | 0.25 | 0 | 0 | 4 | 4 | 0 | 0 | 0 | 0 |
| 7 | 1.0 | 0 | 0 | 5 | 4 | 0 | 0 | 0 | 0 |
| 7 | 0.25 | 0 | 0 | 3 | 0 | 0 | 0 | 0 | 0 |
| 8 | 1.0 | 5 | 5 | 5 | 5 | 0 | 0 | 0 | 0 |
| 8 | 0.25 | 3 | 5 | 5 | 5 | 0 | 0 | 0 | 0 |
| 9 | 1.0 | 5 | 5 | 5 | 5 | 0 | 0 | 0 | 0 |
| 9 | 0.25 | 3 | 5 | 5 | 5 | 0 | 0 | 0 | 0 |
| 10 | 1.0 | 0 | 3 | 5 | 5 | 0 | 0 | 0 | 0 |
| 10 | 0.25 | 0 | 0 | 4 | 5 | 0 | 0 | 0 | 0 |
| 12 | 1.0 | 4 | 5 | 5 | 5 | 0 | 0 | 0 | 0 |
| 12 | 0.25 | 0 | 0 | 5 | 4 | 0 | 0 | 0 | 0 |
| 13 | 1.0 | 0 | 0 | 4 | 4 | 0 | 0 | 0 | 0 |
| 13 | 0.25 | 0 | 0 | 3 | 2 | 0 | 0 | 0 | 0 |
| 15 | 1.0 | 0 | 4 | 5 | 5 | 0 | 0 | 0 | 0 |
| 15 | 0.25 | 0 | 1 | 4 | 4 | 0 | 0 | 0 | 0 |
| 16 | 2.0 | 0 | 0 | 5 | 5 | 0 | 0 | 0 | 0 |
| 16 | 0.5 | 0 | 0 | 5 | 2 | 0 | 0 | 0 | 0 |
| 17 | 2.0 | 0 | 0 | 5 | 4 | 0 | 0 | 0 | 0 |
| 17 | 0.5 | 0 | 0 | 4 | 0 | 0 | 0 | 0 | 0 |
| 18 | 1.0 | 0 | 4 | 5 | 2 | 0 | 0 | 0 | 0 |
| 18 | 0.25 | 0 | 0 | 5 | 0 | 0 | 0 | 0 | 0 |
| 19 | 1.0 | 2 | 5 | 5 | 5 | 0 | 0 | 0 | 0 |
| 19 | 0.25 | 0 | 3 | 5 | 5 | 0 | 0 | 0 | 0 |
| 21 | 1.0 | 0 | 0 | 5 | 5 | 0 | 0 | 0 | 0 |
| 21 | 0.25 | 0 | 0 | 4 | 3 | 0 | 0 | 0 | 0 |
| 22 | 2.0 | 0 | 0 | 5 | 2 | 0 | 0 | 0 | 0 |
| 22 | 0.5 | 0 | 0 | 3 | 0 | 0 | 0 | 0 | 0 |
| 23 | 2.0 | 0 | 0 | 5 | 3 | 0 | 0 | 0 | 0 |
| 23 | 0.5 | 0 | 0 | 2 | 1 | 0 | 0 | 0 | 0 |
| 26 | 0.5 | 0 | 4 | 5 | 5 | 0 | 0 | 0 | 0 |
| 26 | 0.125 | 0 | 1 | 5 | 5 | 0 | 0 | 0 | 0 |
| 27 | 0.5 | 0 | 0 | 3 | 2 | 0 | 0 | 0 | 0 |
| 28 | 0.5 | 0 | 0 | 5 | 5 | 0 | 0 | 0 | 0 |
| 29 | 0.5 | 0 | 0 | 5 | 4 | 0 | 0 | 0 | 0 |
| 30 | 0.5 | 0 | 0 | 5 | 5 | 0 | 0 | 0 | 0 |
| 30 | 0.125 | 0 | 0 | 5 | 5 | 0 | 0 | 0 | 0 |
| 32 | 0.5 | 0 | 4/5 | 5 | 5 | 0 | 0 | 0 | 0 |
| 43 | 0.25 | 0 | 0 | 5 | 5 | 0 | 0 | 0 | 0 |
| 52 | 1.0 | 0 | 3 | 5 | 5 | 0 | 0 | 0 | 0 |
| 53 | 1.0 | 0 | 5 | 5 | 5 | 0 | 0 | 0 | 0 |
| 53 | 0.25 | 0 | 2 | 3 | 4 | 0 | 0 | 0 | 0 |
| 55 | 1.0 | 5 | 5 | 5 | 5 | 0 | 0 | 0 | 0 |
| 55 | 0.25 | 0 | 3 | 5 | 4 | 0 | 0 | 0 | 0 |
| 56 | 1.0 | 1 | 5 | 5 | 5 | 0 | 0 | 0 | 0 |
| 56 | 0.25 | 0 | 4 | 5 | 5 | 0 | 0 | 0 | 0 |
| 57 | 1.0 | 3 | 5 | 5 | 5 | 0 | 0 | 0 | 0 |
| 57 | 0.25 | 0 | 3 | 5 | 5 | 0 | 0 | 0 | 0 |
| 58 | 1.0 | 4 | 4/5 | 5 | 5 | 0 | 0 | 0 | 0 |
| 58 | 0.25 | 0 | 1 | 4 | 4 | 0 | 0 | 0 | 0 |
| 59 | 0.25 | 0 | 3 | 5 | 5 | 0 | 0 | 0 | 0 |
| 60 | 1.0 | 3 | 3 | 5 | 5 | 0 | 0 | 0 | 0 |

TABLE 6-continued

PRE-EMERGENCE HERBICIDAL ACTIVITY

| Compound No | APPLICATION Rate (kg/ha) | Wh | Ot | Rg | Jm | P | Ip | Ms | Sf |
|---|---|---|---|---|---|---|---|---|---|
| 60 | 0.25 | 0 | 0 | 5 | 5 | 0 | 0 | 0 | 0 |
| 62 | 1.0 | 2 | 5 | 5 | 5 | 0 | 0 | 0 | 0 |
| 62 | 0.25 | 0 | 3 | 4 | 5 | 0 | 0 | 0 | 0 |
| 63 | 1.0 | 4 | 5 | 5 | 5 | 0 | 0 | 0 | 0 |
| 64 | 0.25 | 0 | 5 | 5 | 5 | 0 | 0 | 0 | 0 |
| 65 | 1.0 | 3 | 5 | 5 | 5 | 0 | 0 | 0 | 0 |
| 65 | 0.25 | 0 | 5 | 5 | 5 | 0 | 0 | 0 | 0 |
| 66 | 1.0 | 4 | 5 | 5 | 5 | 0 | 0 | 0 | 0 |
| 66 | 0.25 | 1 | 4 | 4 | 5 | 0 | 0 | 0 | 0 |
| 67 | 1.0 | 4 | 4/5 | 5 | 5 | 0 | 0 | 0 | 0 |
| 68 | 1.0 | 3 | 5 | 5 | 5 | 0 | 0 | 0 | 0 |
| 68 | 0.25 | 0 | 3 | 4 | 4 | 0 | 0 | 0 | 0 |
| 69 | 1.0 | 0 | 4 | 4 | 5 | 0 | 0 | 0 | 0 |

EXAMPLE 23

The post-emergent herbicidal activity of the compounds of the invention formulated as described in Example 21 was assessed by the following procedure.

The seeds of the test species were sown in rows 2 cm deep in soil contained in seed boxes. The monocotyledonous plants and the dicotyledonous plants were sown in separate seed boxes in duplicate. The four seed boxes were placed in a glasshouse; lightly watered with an overhead spray to initiate germination and then sub-irrigated as required for optimum plant growth. After the plants had grown to a height of about 10 to 12.5 cm one box of each of the monocotyledonous plants and the dicotyledonous plants was removed from the glasshouse and sprayed with the required quantity of a composition of the invention. After spraying the boxes were returned to the glass house for a further 3 weeks and the effect of treatment was visually assessed by comparison with the untreated controls. The results are presented in Table 7 where the damage to plants is rated on a scale of from 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represents 100% kill. A dash (-) means that no experiment was carried out.

The names of the test plants are as follows:
- Wh  Wheat
- Ot  Wild Oats
- Rg  Ryegrass
- Jm  Japanese millet
- P  Peas
- Ip  Ipomea
- Ms  Mustard
- Sf  Sunflower

TABLE 7

POST-EMERGENCE HERBICIDAL ACTIVITY

| Compound No | APPLICATION Rate (kg/ha) | Wh | Ot | Rg | Jm | P | Ip | Ms | Sf |
|---|---|---|---|---|---|---|---|---|---|
| 1 | 1.0 | 5 | 5 | 5 | 5 | 0 | 0 | 0 | 0 |
| 1 | 0.25 | 1 | 5 | 5 | 5 | 0 | 0 | 0 | 0 |
| 4 | 1.0 | 5 | 5 | 5 | 5 | 0 | 0 | 0 | 0 |
| 4 | 0.25 | 1 | 5 | 5 | 5 | 0 | 0 | 0 | 0 |
| 5 | 1.0 | 0 | 5 | 5 | 5 | 0 | 0 | 0 | 0 |
| 5 | 0.25 | 0 | 4 | 5 | 5 | 0 | 0 | 0 | 0 |
| 6 | 1.0 | 4 | 5 | 5 | 5 | 0 | 0 | 0 | 0 |
| 6 | 0.25 | 0 | 5 | 5 | 5 | 0 | 0 | 0 | 0 |
| 7 | 1.0 | 0 | 4 | 5 | 4 | 0 | 0 | 0 | 0 |
| 7 | 0.25 | 0 | 2 | 4 | 3 | 0 | 0 | 0 | 0 |
| 8 | 1.0 | 5 | 5 | 5 | 5 | 0 | 0 | 0 | 0 |
| 8 | 0.25 | 0 | 5 | 5 | 5 | 0 | 0 | 0 | 0 |
| 9 | 1.0 | 3 | 5 | 5 | 5 | 0 | 0 | 0 | 0 |
| 9 | 0.25 | 0 | 5 | 5 | 5 | 0 | 0 | 0 | 0 |
| 10 | 1.0 | 4 | 5 | 5 | 5 | 0 | 0 | 0 | 0 |
| 10 | 0.25 | 1 | 5 | 5 | 5 | 0 | 0 | 0 | 0 |
| 12 | 1.0 | 0 | 5 | 5 | 5 | 0 | 0 | 0 | 0 |
| 12 | 0.25 | 0 | 4 | 5 | 5 | 0 | 0 | 0 | 0 |
| 13 | 1.0 | 0 | 5 | 5 | 5 | 0 | 0 | 0 | 0 |
| 13 | 0.25 | 0 | 1 | 3 | 4 | 0 | 0 | 0 | 0 |
| 15 | 1.0 | 4 | 5 | 5 | 5 | 0 | 0 | 0 | 0 |
| 15 | 0.25 | 0 | 5 | 5 | 5 | 0 | 0 | 0 | 0 |
| 16 | 2.0 | 2 | 5 | 5 | 5 | 0 | 0 | 0 | 0 |
| 16 | 0.5 | 0 | 0 | 5 | 4 | 0 | 0 | 0 | 0 |
| 17 | 2.0 | 0 | 4 | 5 | 5 | 0 | 0 | 0 | 0 |
| 17 | 0.5 | 0 | 3 | 3 | 4 | 0 | 0 | 0 | 0 |
| 18 | 1.0 | 0 | 5 | 5 | 4 | 0 | 0 | 0 | 0 |
| 18 | 0.25 | 0 | 4 | 4 | 3 | 0 | 0 | 0 | 0 |
| 19 | 1.0 | 0 | 5 | 5 | 5 | 0 | 0 | 0 | 0 |
| 19 | 0.25 | 0 | 5 | 5 | 5 | 0 | 0 | 0 | 0 |
| 21 | 1.0 | 0 | 1 | 4 | 5 | 0 | 0 | 0 | 0 |
| 21 | 0.25 | 0 | 0 | 3 | 4 | 0 | 0 | 0 | 0 |
| 22 | 2.0 | 0 | 0 | 2 | 0 | 0 | 0 | 0 | 0 |
| 22 | 0.5 | 0 | 0 | 0 | 0 | 0 | 0 | 0 | 0 |
| 23 | 2.0 | 0 | 4 | 4 | 4 | 0 | 0 | 0 | 0 |
| 23 | 0.5 | 0 | 3 | 3 | 3 | 0 | 0 | 0 | 0 |
| 26 | 0.5 | 5 | 5 | 5 | 5 | 0 | 0 | 0 | 0 |
| 26 | 0.125 | 5 | 5 | 5 | 5 | 0 | 0 | 0 | 0 |
| 27 | 0.5 | 0 | 5 | 5 | 5 | 0 | 0 | 0 | 0 |
| 27 | 0.125 | 0 | 3 | 5 | 5 | 0 | 0 | 0 | 0 |
| 28 | 0.5 | 3 | 5 | 5 | 5 | 0 | 0 | 0 | 0 |
| 28 | 0.125 | 1 | 5 | 5 | 5 | 0 | 0 | 0 | 0 |
| 29 | 0.5 | 0 | 5 | 3/4 | 5 | 0 | 0 | 0 | 0 |
| 30 | 0.5 | 0 | 3/4 | 5 | 5 | 0 | 0 | 0 | 0 |
| 30 | 0.125 | 0 | 2/3 | 5 | 3 | 0 | 0 | 0 | 0 |
| 31 | 0.125 | 0 | 0 | 4 | 5 | 0 | 0 | 0 | 0 |
| 32 | 0.5 | 4 | 5 | 5 | 5 | 0 | 0 | 0 | 0 |
| 32 | 0.125 | 0 | 4/5 | 5 | 5 | 0 | 0 | 0 | 0 |
| 36 | 0.125 | 0 | 4/5 | 5 | 5 | 0 | 0 | 0 | 0 |
| 40 | 0.25 | 0 | 3/4 | 4/5 | 5 | 0 | 0 | 0 | 0 |
| 41 | 0.25 | 0 | 1 | 3 | 5 | 0 | 0 | 0 | 0 |
| 42 | 0.25 | 0 | 4/5 | 4/5 | 5 | 0 | 0 | 0 | 0 |
| 43 | 0.25 | 0 | 4/5 | 5 | 5 | 0 | 0 | 0 | 0 |
| 46 | 0.25 | 0 | 0 | 3/4 | 5 | 0 | 0 | 0 | 0 |
| 48 | 0.25 | 0 | 4 | 5 | 5 | 0 | 0 | 0 | 0 |
| 50 | 1.00 | 1 | 5 | 5 | 5 | 0 | 0 | 0 | 0 |
| 50 | 0.25 | 0 | 5 | 5 | 5 | 0 | 0 | 0 | 0 |
| 51 | 0.125 | 0 | 2/3 | 4/5 | 5 | 0 | 0 | 0 | 0 |
| 52 | 1.0 | 0 | 4/5 | 5 | 4 | 0 | 0 | 0 | 0 |
| 53 | 1.0 | 5 | 5 | 5 | 5 | 0 | 0 | 0 | 0 |
| 53 | 0.25 | 1 | 5 | 5 | 5 | 0 | 0 | 0 | 0 |
| 54 | 1.0 | 0 | 4/5 | 1 | 0 | 0 | 0 | 0 | 0 |
| 54 | 0.25 | 0 | 4 | 0 | 0 | 0 | 0 | 0 | 0 |
| 55 | 1.0 | 5 | 5 | 5 | 5 | 0 | 0 | 0 | 0 |
| 55 | 0.25 | 5 | 5 | 5 | 5 | 0 | 0 | 0 | 0 |
| 56 | 1.0 | 5 | 5 | 5 | 5 | 0 | 0 | 0 | 0 |
| 56 | 0.25 | 0 | 5 | 5 | 5 | 0 | 0 | 0 | 0 |
| 57 | 1.0 | 4/5 | 5 | 5 | 5 | 0 | 0 | 0 | 0 |
| 57 | 0.25 | 0 | 5 | 5 | 5 | 0 | 0 | 0 | 0 |
| 58 | 1.0 | 5 | 5 | 5 | 5 | 0 | 0 | 0 | 0 |
| 58 | 0.25 | 0 | 5 | 5 | 5 | 0 | 0 | 0 | 0 |
| 59 | 1.0 | 4 | 5 | 5 | 5 | 0 | 0 | 0 | 0 |
| 59 | 0.25 | 0 | 5 | 5 | 5 | 0 | 0 | 0 | 0 |
| 60 | 1.0 | 4 | 5 | 5 | 5 | 0 | 0 | 0 | 0 |
| 60 | 0.25 | 0 | 5 | 5 | 5 | 0 | 0 | 0 | 0 |
| 61 | 1.0 | 1 | 5 | 5 | 5 | 0 | 0 | 0 | 0 |
| 61 | 0.25 | 1 | 5 | 5 | 5 | 0 | 0 | 0 | 0 |
| 62 | 1.0 | 5 | 5 | 5 | 5 | 0 | 0 | 0 | 0 |
| 62 | 0.25 | 0 | 5 | 5 | 5 | 0 | 0 | 0 | 0 |
| 63 | 1.0 | 1 | 5 | 5 | 5 | 0 | 0 | 0 | 0 |
| 63 | 0.25 | 0 | 5 | 5 | 5 | 0 | 0 | 0 | 0 |
| 64 | 1.0 | 1 | 5 | 5 | 5 | 0 | 0 | 0 | 0 |
| 64 | 0.25 | 1 | 5 | 5 | 5 | 0 | 0 | 0 | 0 |
| 65 | 1.0 | 4 | 5 | 5 | 5 | 0 | 0 | 0 | 0 |
| 65 | 0.25 | 0 | 4 | 4 | 4 | 0 | 0 | 0 | 0 |
| 66 | 1.0 | 5 | 5 | 5 | 5 | 0 | 0 | 0 | 0 |
| 66 | 0.25 | 0 | 5 | 5 | 5 | 0 | 0 | 0 | 0 |

TABLE 7-continued

POST-EMERGENCE HERBICIDAL ACTIVITY

| Compound No | APPLICATION Rate (kg/ha) | Wh | Ot | Rg | Jm | P | Ip | Ms | Sf |
|---|---|---|---|---|---|---|---|---|---|
| 67 | 1.0 | 4/5 | 5 | 5 | 5 | 0 | 0 | 0 | 0 |
| 67 | 0.25 | 0 | 5 | 5 | 5 | 0 | 0 | 0 | 0 |
| 68 | 1.0 | 5 | 5 | 5 | 5 | 0 | 0 | 0 | 0 |
| 68 | 0.25 | 0 | 5 | 5 | 5 | 0 | 0 | 0 | 0 |
| 69 | 1.0 | 1 | 5 | 5 | 5 | 0 | 0 | 0 | 0 |
| 69 | 0.25 | 0 | 5 | 5 | 5 | 0 | 0 | 0 | 0 |
| 70 | 1.0 | 0 | 5 | 5 | 5 | 0 | 0 | 0 | 0 |
| 70 | 0.25 | 0 | 5 | 0 | 5 | 0 | 0 | 0 | 0 |
| 71 | 1.0 | 0 | 5 | 5 | 5 | 0 | 0 | 0 | 0 |
| 71 | 0.25 | 0 | 3/4 | 1 | 0 | 0 | 0 | 0 | 0 |
| 72 | 1.0 | 0 | 2 | 3 | 5 | 0 | 0 | 0 | 0 |
| 73 | 1.0 | 0 | 5 | 5 | 5 | 0 | 0 | 0 | 0 |

EXAMPLE 24

The compounds were formulated for test by mixing an appropriate amount with 5 ml of an emulsion prepared by diluting 160 ml of a solution containing 21.9 g per liter of "Span" 80 and 78.2 g per liter of "Tween" 20 in methylcyclohexanone to 500 ml with water. "Span" 80 is a Trade Mark for a surface-active agent comprising sorbitan monolaurate. "Tween" 20 is a Trade Mark for a surface-active agent comprising a condensate of sorbitan monolaurate with 20 molar proportions of ethylene oxide. Each 5 ml emulsion containing a test compound was then diluted to 40 ml with water and sprayed on to young pot plants (post-emergence test) of the species named in Table 8 below. Damage to test plants was assessed after 14 days on a scale of 0 to 5 where 0 is 0 to 20% damage and 5 is complete kill. In a test for post-emergence herbicidal activity, seeds of the test plants were sown in a shallow slit formed in the surface of soil in fibre trays. The surface was then levelled and sprayed, and fresh soil then spread thinly over the sprayed surface. Assessment of herbicidal damage was carried out after 21 days using the same scale of 0 to 5 as the post-emergence test. In both cases the degree of herbicidal damage was assessed by comparison with untreated control plants. The results are given in Table 8 below. A dash (-) means that no experiment was carried out.

The names of the test plants were as follows:

| | |
|---|---|
| Sb | Sugar Beet |
| Rp | Rape |
| Ct | Cotton |
| Sy | Soy bean |
| Mz | Maize |
| Ww | Winter wheat |
| Rc | Rice |
| Sn | *Senecio vulgaris* |
| Ip | *Ipomea purpurea* |
| Am | *Amaranthus retroflexus* |
| Pi | *Polygonum aviculare* |
| Ca | *Chenopodium album* |
| Ga | *Galium aparine* |
| Xa | *Xanthium pensylvanicum* |
| Ab | *Abutilon theophrasti* |
| Co | *Cassia obtusifolia* |
| Av | *Avena fatua* |
| Dg | *Digitaria sanguinalis* |
| Al | *Alopecurus myosuroides* |
| St | *Setaria viridis* |
| Ec | *Echinochloa crus-galli* |
| Sh | *Sorghum halepense* |
| Ag | *Agropyron repens* |
| Cn | *Cyperus rotundas* |

TABLE 8

PART A

| Compound No | APPLICATION Method | Rate (kg/ha) | Sb | Rp | Ct | Sy | Mz | Ww | Rc | Sn | Ip | Am | Pi | Ca |
|---|---|---|---|---|---|---|---|---|---|---|---|---|---|---|
| 4 | PRE | 0.4 | — | — | — | — | 4 | 5 | 5 | — | — | — | — | — |
| 4 | PRE | 0.1 | — | — | — | — | 4 | 3 | 5 | — | — | — | — | — |
| 4 | POST | 0.4 | — | — | — | — | 5 | 1 | 4 | — | — | — | — | — |
| 4 | POST | 0.1 | — | — | — | — | 4 | 0 | 4 | — | — | — | — | — |
| 40 | PRE | 0.2 | — | — | — | — | 5 | 4 | 5 | — | — | — | — | — |
| 40 | PRE | 0.05 | — | — | — | — | 3 | 0 | 3 | — | — | — | — | — |
| 40 | POST | 0.2 | — | — | — | — | 5 | 2 | 4 | — | — | — | — | — |
| 40 | POST | 0.05 | — | — | — | — | 2 | 0 | 2 | — | — | — | — | — |
| 42 | PRE | 0.05 | — | — | — | — | 4 | 1 | 5 | — | — | — | — | — |
| 42 | POST | 0.2 | — | — | — | — | 5 | 0 | 4 | — | — | — | — | — |
| 47 | PRE | 0.4 | — | — | — | — | 4 | 5 | 5 | — | — | — | — | — |
| 47 | POST | 0.1 | — | — | — | — | 5 | 0 | 0 | — | — | — | — | — |
| 47 | POST | 0.05 | — | — | — | — | 5 | 0 | 1 | — | — | — | — | — |
| 58 | PRE | 0.2 | — | — | — | — | 4 | 3 | 5 | — | — | — | — | — |
| 58 | PRE | 0.05 | — | — | — | — | 2 | 1 | 3 | — | — | — | — | — |
| 58 | POST | 0.2 | — | — | — | — | 5 | 1 | 3 | — | — | — | — | — |
| 58 | POST | 0.05 | — | — | — | — | 5 | 0 | 1 | — | — | — | — | — |
| 59 | PRE | 0.05 | — | — | — | — | 4 | 1 | 3 | — | — | — | — | — |
| 59 | POST | 0.05 | — | — | — | — | 5 | 0 | 2 | — | — | — | — | — |

PART B

| Compound No. | APPLICATION Method | Rate (kg/ha) | Ga | Xa | Ab | Co | Av | Dg | Al | St | Ec | Sh | Ag | Cn |
|---|---|---|---|---|---|---|---|---|---|---|---|---|---|---|
| 4 | PRE | 0.4 | — | — | — | — | 5 | 5 | 5 | 5 | 5 | 4 | 5 | — |
| 4 | PRE | 0.1 | — | — | — | — | 5 | 4 | 5 | 5 | 4 | 1 | — | — |
| 4 | POST | 0.4 | — | — | — | — | 4 | 4 | 4 | 5 | 5 | 2 | — | — |
| 4 | POST | 0.1 | — | — | — | — | 4 | 3 | 3 | 4 | 4 | 0 | — | — |
| 40 | PRE | 0.2 | — | — | — | — | 5 | 5 | 5 | 5 | 5 | 4 | 5 | — |
| 40 | PRE | 0.05 | — | — | — | — | 4 | 4 | 5 | 4 | 1 | 2 | 5 | — |
| 40 | POST | 0.2 | — | — | — | — | 5 | 5 | 4 | 5 | 5 | 3 | — | — |
| 40 | POST | 0.05 | — | — | — | — | 3 | 4 | 4 | 4 | 3 | 1 | — | — |
| 42 | PRE | 0.05 | — | — | — | — | 5 | 4 | 5 | 5 | 4 | 5 | — | — |

TABLE 8-continued

| | | PART A | | | | | | | | | | | | |
|---|---|---|---|---|---|---|---|---|---|---|---|---|---|---|
| 42 | POST | 0.2 | — | — | — | — | 5 | 5 | 5 | 5 | 5 | 5 | 1 | — |
| 47 | PRE | 0.4 | — | — | — | — | 4 | 5 | 5 | 4 | 4 | 5 | — | |
| 47 | PRE | 0.1 | — | — | — | — | 3 | 4 | 5 | 3 | 0 | 4 | 2 | — |
| 47 | POST | 0.1 | — | — | — | — | 4 | 4 | 4 | 4 | 4 | 3 | 0 | — |
| 47 | POST | 0.05 | — | — | — | — | 4 | 4 | 4 | 4 | 4 | 3 | 0 | — |
| 58 | PRE | 0.2 | — | — | — | — | 4 | 5 | 5 | 3 | 0 | 4 | 5 | — |
| 58 | PRE | 0.05 | — | — | — | — | 3 | 2 | 3 | 0 | 0 | 2 | 5 | — |
| 58 | POST | 0.2 | — | — | — | — | 5 | 5 | 5 | 5 | 5 | 5 | 0 | — |
| 58 | POST | 0.05 | — | — | — | — | 5 | 4 | 4 | 4 | 4 | 4 | 0 | — |
| 59 | PRE | 0.05 | — | — | — | — | 3 | 5 | 5 | 3 | 2 | 1 | 5 | — |
| 59 | POST | 0.05 | — | — | — | — | 5 | 4 | 4 | 5 | 5 | 4 | 0 | — |

EXAMPLE 25

This Example illustrates the selective herbicidal activity of compounds of the invention.

The compounds were formulated for test by mixing an appropriate amount with 5 ml of an emulsion prepared by diluting 160 ml of a solution containing 21.8 g per liter of "Span" 80 and 78.2 g per liter of "Tween" 20 in methylcyclohexanone to 500 ml with water. "Span" 80 is a Trade Mark for a surface-active agent comprising sorbitan monolaurate. "Tween" 20 is a Trade Mark for a surface-active agent comprising a condensate or sorbitan monolaurate with 20 molar proportions of ethylene oxide. Each 5 ml emulsion containing a test compound was then diluted to 40 ml with water and sprayed on to young pot plants (post-emergence test) of the species named in Table 9 below. Damage to test plants was assessed after 26 days on a scale of 0 to 9 where 0 is 0 to 10% damage and 9 is a complete kill. The degree of herbicidal damage was assessed by comparison with untreated control plants and the results are given in Table 9 below. A dash (-) means that no experiment was carried out.

The names of the test plants were as follows:
Ww   winter wheat
Br   spring barley
Av   *Avena fatua*
Al   *Alopecurus myosuroides*
St   *Setaria viridis*

TABLE 9
POST-EMERGENCE HERBICIDAL ACTIVITY

| Compound No | APPLICATION Rate (kg/ha) | TEST PLANT | | | | |
|---|---|---|---|---|---|---|
| | | Ww | Br | Av | Al | St |
| 4 | 0.04 | — | — | 9 | 6 | 7 |
| 4 | 0.06 | 0 | 0 | 9 | 7 | 8 |
| 4 | 0.08 | 0 | 0 | 9 | 8 | 8 |
| 4 | 0.16 | 0 | 1 | — | — | — |
| 14 | 0.08 | — | — | 9 | 7 | 9 |
| 14 | 0.12 | 0 | 0 | 9 | 9 | 9 |
| 14 | 0.16 | 0 | 0 | 9 | 8 | 9 |
| 32 | 0.02 | — | — | 8 | 8 | 9 |
| 32 | 0.04 | — | — | 9 | 8 | 9 |
| 32 | 0.06 | 1 | 0 | 9 | 9 | 9 |
| 45 | 0.02 | — | — | 9 | 9 | 9 |
| 45 | 0.04 | — | — | 9 | 9 | 9 |
| 45 | 0.06 | 1 | 1 | 9 | 9 | 9 |

We claim:
1. A compound of the formula

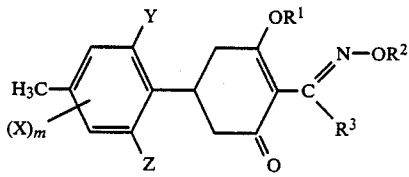

wherein:
Z and Y are independently selected from the group consisting of fluorine, chlorine, bromine, methyl, and methoxy;
X, which may be the same or different if there is more than one X, is selected from the group consisting of fluorine, chlorine, bromine, methyl, ethyl and methoxy;
at least one of Z, Y and X is methyl and if Z and Y are both methyl then at least on of X is not methyl;
$R^1$ is selected from the group consisting of hydrogen, benzoyl, lithium, sodium and potassium;
$R^2$ is selected from the group consisting of; $C_1$ and $C_6$ alkyl; $C_2$ to $C_6$ alkenyl; $C_3$ to $C_6$ alkynyl; $C_1$ to $C_6$ haloalkyl; $C_2$ to $C_6$ haloalkenyl; and $C_3$ to $C_6$ haloalkynyl;
$R^3$ is selected from the group consisting of $C_1$ to $C_6$ alkyl;
m is selected from 0, 1 and 2.

2. A compound according to claim 1 of formula

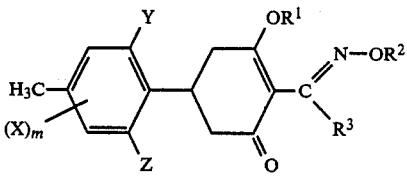

wherein:
Z and Y are independently selected from the group consisting of fluorine, chlorine, bromine, methyl, and methoxy;
X, which may be the same or different if there is more than one X, is selected from the group consisting of fluorine, chlorine, bromine, methyl, ethyl and methoxy;
at least one of Z, Y and X is methyl and if Z and Y are both methyl then at least one of X is not methyl;
$R^1$ is selected from the group consisting of hydrogen, benzoyl, lithium, sodium and potassium;
$R^2$ is selected from ethyl and allyl;
$R^3$ is selected from ethyl and n-propyl; and
m is selected from 0, 1 and 2.

3. A compound according to claim 2 of formula

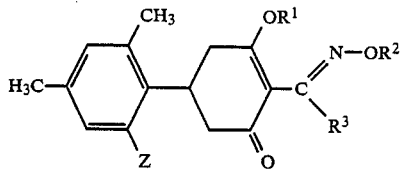

wherein:

Z is selected from the group consisting of fluoro, chloro, bromo and methoxy;

R$^1$ is selected from the group consisting of hydrogen, sodium and potassium;

R$^2$ is selected from ethyl and allyl; and

R$^3$ is selected from ethyl and n-propyl.

4. A compound according to claim 2 of formula

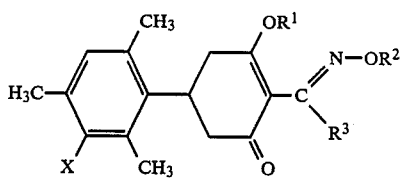

wherein:

X is selected from the group consisting of fluorine, chlorine and bromine;

R$^1$ is selected from the group consisting of hydrogen, sodium and potassium;

R$^2$ is selected from ethyl and allyl; and

R$^3$ is selected from ethyl and n-propyl.

5. A compound according to claim 2 of formula

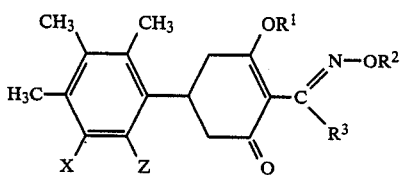

wherein:

X and Z are independently selected from the group consisting of fluorine, chlorine, bromine and methyl;

one of X and Z is selected from the group consisting of fluorine, chlorine and bromine;

R$^1$ is selected from the group consisting of hydrogen, sodium and potassium;

R$^2$ is selected from ethyl and allyl; and

R$^3$ is selected from ethyl and n-propyl.

6. A compound according to claim 2 selected from the group consisting of:

2-[1-(ethoxyimino)propyl]-3-hydroxy-5-(2-methoxy-4,6-dimethylphenyl)cyclohex-2-en-1-one;

2-[1-(ethoxyimino)butyl]-3-hydroxy-5-(2-methoxy-4,6-dimethylphenyl)cyclohex-2-en-1-one;

2-[1-(ethoxyimino)butyl]-3-hydroxy-5-(2-chloro-3,4,5,6-tetramethylphenyl)cyclohex-2-en-1-one;

2-[1-(ethoxyimino)butyl]-3-hydroxy-5-(2-bromo-3,4,5,6-tetramethylphenyl)cyclohex-2-en-1-one;

2-[1-(ethoxyimino)butyl]-3-hydroxy-5-(3-fluoro-2,4,6-trimethylphenyl)cyclohex-2-en-1-one;

2-[1-(ethoxyimino)butyl]-3-hydroxy-5-(3-chloro-2,4,6-trimethylphenyl)cyclohex-2-en-1-one; and 2-[1-(ethoxyimino)butyl]-3-hydroxy-5-(3-fluoro-2,4,5,6-tetramethylphenyl)cyclohex-2-en-1-one.

7. A herbicidal composition comprising as active ingredient a herbicidally effective amount of a compound as defined according to claim 1 and a carrier therefor.

8. A process for severely damaging or killing unwanted plants which process comprises applying to said plants, or to the growth medium of said plants, an effective amount of a compound as defined according to claim 1.

9. A process for selectively controlling the growth of monocotyledonous weeds in dicotyledonous crops which process comprises applying to said crop, or to the growth medium of said crop, a compound as defined according to claim 1 in an amount sufficient to severely damage or kill said weeds but insufficient to substantially damage said crop.

10. A process for selectively controlling the growth of monocotyledonous weeds in cultivated crops which process comprises applying to said crop or to the growth medium of said crop a compound as defined according to claim 1 in an amount sufficient to severely damage or kill said weeds but insufficient to substantially damage said crop.

11. A process according to claim 8 wherein the compound is applied at a rate in the range of from 0.005 to 20 kilograms per hectare.

12. A process according to claim 9 wherein the compound is applied at a rate in the range of from 0.01 to 5 kilograms per hectare.

13. A process according to claim 10 wherein the compound is applied at a rate in the range of from 0.01 to 5 kilograms per hectare.

* * * * *